(12) United States Patent
Arsenjans et al.

(10) Patent No.: US 10,561,681 B2
(45) Date of Patent: Feb. 18, 2020

(54) ANTIMETASTATIC 2H-SELENOPHENO[3,2-H]CHROMENES, SYNTHESIS THEREOF, AND METHODS OF USING SAME AGENTS

(71) Applicant: Latvian Institute of Organic Synthesis, Riga (LV)

(72) Inventors: Pavels Arsenjans, Riga (LV); Jelena Vasiljeva, Riga (LV); Ilona Domracheva, Riga (LV); Irina Shestakova, Riga (LV); Ivars Kalvins, Ikskile (LV)

(73) Assignee: Latvian Institute of Organic Synthesis, Riga (LV)

( * ) Notice: Subject to any disclaimer, the term of this patent is extended or adjusted under 35 U.S.C. 154(b) by 0 days.

(21) Appl. No.: 16/315,264

(22) PCT Filed: Jul. 21, 2016

(86) PCT No.: PCT/IB2016/054341
§ 371 (c)(1),
(2) Date: Jan. 4, 2019

(87) PCT Pub. No.: WO2018/015788
PCT Pub. Date: Jan. 25, 2018

(65) Prior Publication Data
US 2019/0298758 A1 Oct. 3, 2019

(51) Int. Cl.
*A61K 33/04* (2006.01)
*C07D 517/14* (2006.01)
*C07D 517/04* (2006.01)

(52) U.S. Cl.
CPC ............ *A61K 33/04* (2013.01); *C07D 517/04* (2013.01); *C07D 517/14* (2013.01)

(58) Field of Classification Search
CPC ..................................................... A61K 33/04

USPC .......................................................... 549/381
See application file for complete search history.

(56) References Cited

PUBLICATIONS

Arsenyan, P., et al., "Selenopheno[3,2-c]- and [2,3-c]coumarins: Synthesis, cytotoxicity, angiogenesis inhibition, and -antioxidant properties," Omptes Rendus Chim IE., vol. 18, No. 4, Apr. 1, 2015 (Apr. 1, 2015), pp. 399-409.

Arsenyan, P., et al., "Synthesis and molecular structure of the methyl ester of 3-bromo-2-(2-hydroxy-2-propyl)-7-oxo-7H-selenolo[2,3-f]chromene-8-carboxylic acid11," Chemistry of Heterocyclic Compounds, vol. 47, No. 2, May 1, 2011 (May 1, 2011), pp. 237-241.

International Search Report mailed in International Application No. PCT/IB2016/054341 (dated Sep. 12, 2016).

*Primary Examiner* — Taofiq A Solola
(74) *Attorney, Agent, or Firm* — Fish & Richardson P.C.

(57) ABSTRACT

The present invention relates to a novel cancer metastasis preventing and curing selenopheno[h]chromene derivatives, as well as methods of their manufacturing and use in different pharmaceutical compositions for the treatment and/ or prevention of primary cancer and its metastasis by administration of such substances.

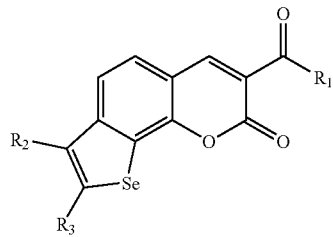

17 Claims, 1 Drawing Sheet

ANTIMETASTATIC 2H-SELENOPHENO[3,2-H]CHROMENES, SYNTHESIS THEREOF, AND METHODS OF USING SAME AGENTS

CROSS REFERENCE TO RELATED APPLICATION

This application is a U.S. national phase filing under 35 U.S.C. § 371 of International Application No. PCT/IB2016/054341, filed Jul. 21, 2016. The International Application was published in English on Jan. 25, 2018 as WO 2018/015788 under PCT Article 21(2). The entire contents of the prior application are incorporated herein by reference in their entirety.

FIELD OF THE INVENTION

Embodiments herein relate to the field of chemistry and biochemistry, and, more specifically, to anti-cancer compounds, synthesis thereof, and methods of using same. The present invention discloses novel 2H-selenopheno[3,2-h]chromene derivatives, a process of the manufacture and the use of the disclosed compounds for treatment and/or prevention of cancer and metastasis.

BACKGROUND OF THE INVENTION

Cancers of different localization are widespread and are major cause of mortality of all ages. Tumor growth is a complex multistage process. Occurrence and progressive tumor growth is dependent on both the properties of cancer cells, and the state of immunological reactivity. This determines the diversity of approaches of the cancer therapy using one or several basic methods: surgery, radiotherapy, chemotherapy and immunotherapy. Their goal is to minimize the mass of the tumor. In case of solid tumors, surgical removal of the tumor is the first line option. Leukemia and other generalized diseases are treated by massive radiation or chemotherapy. However, neither method alone is able to eliminate all tumor cells and to achieve a total recovery. Therefore, modern oncology usually applies the combinations of treatments to eliminate the tumor cells.

Unfortunately, in spite of the successful surgical removal of the primary tumor, the likelihood of recurrence is very high, since the tumor is able to spread and metastasize to surrounding tissues and organs. Metastasis begins with local invasion of tumor cells from the primary tumor into the surrounding tissue and cells enter the blood or lymphatic circulation system (Hunter, et al, Breast Cancer Res, 2008, 10, S2; Talmadge et al, Cancer Res 2010, 70, 5649-5669). After removal of the primary tumor the percentage of patients who have diagnosed metastases in various organs is up to 30% (Essner et al, Arch Surg, 2004, 139, 961-966, 966-7).

Metastases are responsive for 90% of deaths from cancer. There are the lymphogenous, hematogenous and mixed (through lymphatic, haematogenous or through seeding) ways of spreading metastasis. Lymphogenous spreading occurs through the lymphatic system, where cancer cells penetrate the lymphatic system and then enter the blood stream. Malignant tumors of internal organs: esophagus, stomach, colon, larynx, cervix—often metastasize to the lymph nodes in this way.

In the case of haematogenous path, the tumor cells penetrate the blood vessel first and then disseminate by blood flow in different organs and tissues (e.g. lungs, liver, bone etc.). Most deaths associated with this pathway, because surgical intervention increases the risk of the spread of tumor cells from the bloodstream. Malignant tumors of the lymphatic and hematopoietic tissue—sarcoma, hypernephroma, horionepitelioma metastasize in this way.

However, most cancers: breast, thyroid, lungs and ovaries—are able to metastasize by lymphogenous and haematogenous equally (Achen, Stacker, Annals of the New York Academy of Sciences, 2008, 1131, pp. 225-234; Li and Li, Int. J. Oncol., 2014, 44, 1806-1812).

Metastatic cancer may be treated with systemic therapy (chemotherapy, biological therapy, targeted therapy, hormonal therapy), local therapy (surgery, radiation therapy), or a combination of these treatments. ([Guideline] Fizazi K, Greco F A, Pavlidis N, Daugaard G, Oien K, Pentheroudakis G, et al. Cancers of unknown primary site: ESMO Clinical Practice Guidelines for diagnosis, treatment and follow-up. *Ann Oncol.* 2015 Sep. 26 Suppl. 5:v133-8.) Several anti-cancer drugs like oxaliplatin and irinotecan are used in liver metastasis with some effect. Efficiency of the treatment of metastatic cancer of unknown primary origin with cisplatin and 5-fluorouracil-based chemotherapy is still under debate. The most effective chemotherapy regimens for patients with metastatic cancer of unknown primary origin involve combination therapy with a platinum compound (cisplatin or carboplatin) and a taxane (preferably paclitaxel). However, even this combination gives a response rate only of about 12-26% and a median survival of 5-7 months. Triple drug therapy does not appear to offer any additional benefit (Vajdic C M, Goldstein D. Cancer of unknown primary site. *Aust Famr Physician.* 2015 September 44 (9):640-3.)

Unfortunately, majority of metastatic cancers are not curable today. For example, metastatic breast cancer treatment can prolong life, delay the progression of the cancer, relieve cancer-related symptoms, and improve quality of life. Nevertheless, the median survival of individuals with metastatic breast cancer is only 18 to 24 months (http://www.uptodate.com/contents/treatment-of-metastatic-breast-cancer-beyond-the-basics). Therefore, there still is high medical need for effective antimetastatic chemotherapeutic medicines.

THE PRESENT INVENTION

We have surprisingly discovered that certain novel 2H-selenopheno[3,2-h]chromene derivatives with low or medium cytotoxicity on cancer cell lines unexpectedly have excellent antimetastatic activity in vivo against various cancers. These substances are highly appropriate for the treatment and/or prevention of metastatic tumors because of extremely low cytotoxicity against normal mouse embryo fibroblasts. These novel compounds can be used for manufacturing of a various pharmaceutical composition, wherein they are present together with one or more pharmaceutically acceptable diluents, carriers, or excipients.

OBJECTS OF THE INVENTION

An object of the present invention are selenium containing novel compounds with anticancer properties, useful for treatment of primary cancers and/or metastasis of them, methods for manufacturing of disclosed compounds and the treatment and/or prevention of various cancers by administration of such substances.

SUMMARY OF THE INVENTION

We disclosed compounds selected from those of Formula I

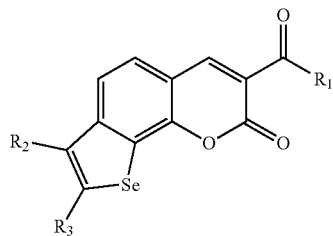

wherein $R_1$ represents OH or an $OC_1$-$C_{16}$ hydrocarbon group, including steroid moiety (e.g. cholesterol), N(alkyl)$_2$, or N-heterocyclyl;

$R_2$ represents a halogen atom (e.g. Br); and $R_3$ represents hydroxy-$C_{1-4}$alkyl, 1-hydroxy-cyclo-$C_{3-6}$alkyl, cyclo-$C_{5-7}$alkenyl, hydroxy-$C_{1-6}$cycloalkyl, or $C_{1-4}$alkyl-N-heterocyclyl.

As used herein, the term "hydrocarbon" refers to a cyclic, branched, or straight chain alkyl group, an alkenyl group, or an alkynyl group. Hydrocarbon-groups can either be unsubstituted or substituted with one or more substituents. If the hydrocarbon is a branched structure having substituent(s) thereon, then the substitution may be on either the hydrocarbon backbone or on the branch; alternatively, the substitutions may be on the hydrocarbon backbone and on the branch.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. The term "alkylene" refers to a divalent alkyl, e.g., —CH$_2$—, —CH$_2$CH$_2$—, —CH$_2$CH$_2$CH$_2$— or —CH$_2$CH(CH$_3$)CH$_2$—. An alkyl or alkylene may be optionally substituted.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH═CH—, —CH═CH$_2$CH$_2$— or —CH═C═CH—. An alkenyl or alkenylene may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—CH$_2$—. An alkynyl or alkynylene may be optionally substituted.

As used herein, the term "ester" refers to the product of the reaction between a carboxylic acid and an alcohol.

As used herein, the term "amide" refers to an organic compound containing the —CONH$_2$— group.

As used herein, the term "aryl" refers to phenyl and naphthyl.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents).

Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

As used herein, the term "halo" or "halogen" refers to fluorine, chlorine, bromine and iodine.

Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

Specific compounds of Formula I within the present invention include but are not limited to:

methyl 7-bromo-8-(2-hydroxypropan-2-yl)-2-oxo-2H-selenopheno[3,2-h]chromene-3-carboxylate, methyl 7-bromo-8-(cyclopent-1-en-1-yl)-2-oxo-2H-selenopheno[3,2-h]chromene-3-carboxylate, methyl 7-bromo-8-(1-hydroxycyclohexyl)-2-oxo-2H-selenopheno[3,2-h]chromene-3-carboxylate, methyl 7-bromo-8-(1-methoxycyclohexyl)-2-oxo-2H-selenopheno[3,2-h]chromene-3-carboxylate, butyl 7-bromo-8-(1-methoxycyclohexyl)-2-oxo-2H-selenopheno[3,2-h]chromene-3-carboxylate, octyl 7-bromo-8-(1-methoxycyclohexyl)-2-oxo-2H-selenopheno[3,2-h]chromene-3-carboxylate, decyl 7-bromo-8-(1-methoxycyclohexyl)-2-oxo-2H-selenopheno[3,2-h]chromene-3-carboxylate, methyl 7-bromo-2-oxo-8-(piperidin-1-ylmethyl)-2H-selenopheno[3,2-h]chromene-3-carboxylate, methyl 7-bromo-8-(morpholinomethyl)-2-oxo-2H-selenopheno[3,2-h]chromene-3-carboxylate, methyl 7-bromo-8-((4-methylpiperazin-1-yl)methyl)-2-oxo-2H-selenopheno[3,2-h]chromene-3-carboxylate, 7-bromo-8-(1-hydroxycyclohexyl)-2-oxo-2H-selenopheno[3,2-h]chromene-3-carboxylic acid, 7-bromo-8-(1-methoxycyclohexyl)-2-oxo-2H-selenopheno[3,2-h]chromene-3-carboxylic acid, 7-bromo-2-oxo-8-(piperidin-1-ylmethyl)-2H-selenopheno [3,2-h]chromene-3-carboxylic acid hydrochloride,
7-bromo-2-oxo-8-(morpholin-1-ylmethyl)-2H-selenopheno [3,2-h]chromene-3-carboxylic acid hydrochloride,
7-bromo-8-((4-methylpiperazin-1-yl)methyl)-2-oxo-2H-selenopheno[3,2-h]chromene-3-carboxylic acid hydrochloride,
octyl 7-bromo-8-(cyclohex-1-en-1-yl)-2-oxo-2H-selenopheno[3,2-h]chromene-3-carboxylate,
(3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl-7-bromo-8-(cyclohex-1-en-1-yl)-2-oxo-2H-selenopheno[3,2-h]chromene-3-carboxylate,
(3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl-7-bromo-8-(1-methoxycyclohexyl)-2-oxo-2H-selenopheno [3,2-h]chromene-3-carboxylate,
7-bromo-8-(cyclohex-1-en-1-yl)-3-(piperidine-1-carbonyl)-2H-selenopheno[3,2-h]chromen-2-one,
7-bromo-8-(cyclohex-1-en-1-yl)-3-(morpholine-1-carbonyl)-2H-selenopheno[3,2-h]chromen-2-one,
7-bromo-8-(cyclohex-1-en-1-yl)-N,N-bis(2-methoxyethyl)-2-oxo-2H-selenopheno[3,2-h]chromene-3-carboxamide,
7-bromo-8-(1-methoxycyclohexyl)-3-(morpholine-4-carbonyl)-2H-selenopheno[3,2-h]chromen-2-one.

DETAILED DESCRIPTION OF THE INVENTION

Figure 1:
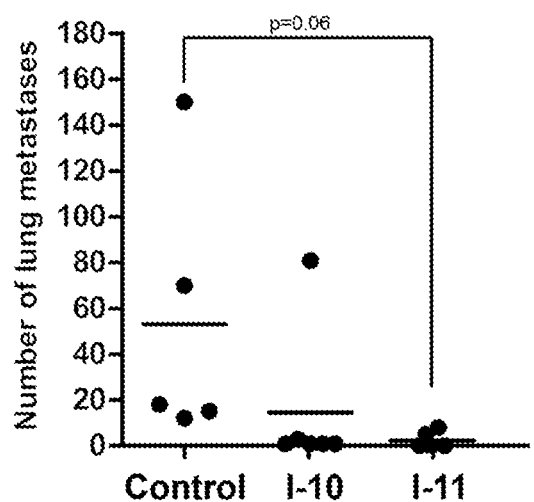
FIG. 1 is a graph demonstrating the inhibition of B16-F10 metastasis in lung (C57BL/6 mice). B16-F10 cells (10,000/0.1 ml PBS) were injected i.v. into syngeneic mice. The number of macroscopic lung metastases was determined 21 days later.

Searching for anticancer compounds with antimetastatic properties we unexpectedly discovered that 2H-selenopheno [3,2-h]chromene derivatives of Formula 1 are highly active against developing of metastasis of various tumors in experimental animals. It was surprisingly also that these compounds were highly selective against cancer cells without significant cytotoxicity against normal 3T3 cells (mouse embryo fibroblasts), widely used for in vitro estimation of LD50. Our finding is unexpected, because it is well known, that high toxicity and low selectivity against cancer cells versus normal cells are typical for selenium containing molecules.

Historically selenium has attracted great interest as an essential microelement. Certain diseases can be controlled by dietary supplementation of this element. Selenium is essential for cell metabolism as a component of glutathione peroxidase and other enzyme systems. There are some attempts to use Se-containing supplements in the prevention of certain cancers. Unfortunately, selenium containing compounds anticancer activity is still unpredictable because based on several mechanisms depending on the chemical form of selenium and structural features of designed compounds. Even if these compounds are active in cell lines, there is lack of rules predicting basal toxicity and selectivity as well as antimetastatic activity of the novel Se-containing compounds in vivo.

We discovered that antimetastatic activity is typical for a number of compounds with 2H-selenopheno[3,2-h] chromene backbone, especially if there are substituents present in positions 7 and 8 of this scaffold. We found that the most appropriate substituents for $R_2$ in position 7 of compounds according to Formula 1 are halogens, as well as for $R_3$ in the position 8 most preferable were hydroxy-$C_{1-4}$ alkyl, 1-hydroxy-cyclo-$C_{3-6}$alkyl, cyclo-$C_{5-7}$alkenyl, hydroxy-$C_{1-6}$cycloalkyl, or $C_{1-4}$alkyl-N-heterocyclyl groups.

Acid, ester or amide moiety will be preferred in position 3 of compounds represented by Formula 1.

We discovered also, that substituents $R_1$ could be preferably selected from group of substituents consisting of OH and an $OC_1$-$C_{16}$ hydrocarbon group, including steroid moiety (e.g. cholesterol), N(alkyl)$_2$, and N-heterocyclyl-moiety.

As used herein, the term "hydrocarbon" refers to a cyclic, branched, or straight chain alkyl group, an alkenyl group, or an alkynyl group. Hydrocarbon-groups can either be unsubstituted or substituted with one or more substituents. If the hydrocarbon is a branched structure having substituent(s) thereon, then the substitution may be on either the hydrocarbon backbone or on the branch; alternatively, the substitutions may be on the hydrocarbon backbone and on the branch.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms. The term "alkylene" refers to a divalent alkyl, e.g., —CH$_2$—, —CH$_2$CH$_2$—, —CH$_2$CH$_2$CH$_2$— or —CH$_2$CH(CH$_3$) CH$_2$—. An alkyl or alkylene may be optionally substituted.

The term "cycloalkyl" as used herein refers to nonaromatic, saturated or partially unsaturated cyclic, bicyclic, tricyclic or polycyclic hydrocarbon groups having 3 to 12 carbons.

Any ring atom can be substituted (e.g., with one or more substituents). Cycloalkyl groups can contain fused rings. Fused rings are rings that share one or more common carbon atoms.

Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH=CH—, —CH=CH$_2$CH$_2$— or —CH=C=CH—. An alkenyl or alkenylene may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—CH$_2$—. An alkynyl or alkynylene may be optionally substituted.

As used herein, the term "ester" refers to the product of the reaction between a carboxylic acid and an alcohol.

As used herein, the term "amide" refers to an organic compound containing the —CONH$_2$— group.

As used herein, the term "aryl" refers to phenyl and naphthyl.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents).

Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

As used herein, the term "halo" or "halogen" refers to fluorine, chlorine, bromine and iodine.

Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

The term "pharmaceutically acceptable" refers here to the therapeutically active non-toxic salt forms, which the compounds of Formula I are able to form. The latter can conveniently be obtained by treating the base form with such appropriate acids as inorganic acids such as hydrochloric acid, hydrobromic acid; sulfuric acid; nitric acid; phosphoric acid and the like; or organic acids such as acetic, propanoic, hydroxyacetic, 2-hydroxypropanoic, oxopropanoic, oxalic, malonic, succinic, maleic, fumaric, malic, tartaric, methanesulfonic, benzenesulfonic, 4-methylbenzenesulfonic, 2-hydroxybenzoic, and like acids. Conversely, the salt may be converted to the free base by treatment with alkali.

For therapeutic use, the compounds of Formula I can be in the form of a solvate.

Pharmaceutical compositions in accordance with embodiments of the disclosure may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds disclosed herein dissolved in water and water-propylene glycol systems, optionally containing suitable conventional coloring agents, flavoring agents, stabilizers, and/or thickening agents.

In an embodiment, a pharmaceutical composition may be provided employing conventional techniques in unit dosage form containing effective or appropriate amounts of one or more active component. In embodiments, the quantity of active component (compound) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

In embodiments, in therapeutic use for treating, ameliorating, preventing, or combating cancer in animals, the compounds or pharmaceutical compositions thereof may be administered orally, parenterally, topically, and/or by inhalation at a dosage to obtain and maintain a concentration or blood-level of active component in the animal undergoing treatment that is therapeutically effective. In an embodiment, such a therapeutically effective amount of dosage of active component may be in the range of about 0.1 to about 100 mg/kg, more preferably about 3.0 to about 50 mg/kg, of body weight/day. It is to be understood that the dosages may vary depending upon the requirements of the patient, the severity, type, stage, grade, or location of the cancer being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose also may be divided into multiple doses for administration, for instance, two to four times per day.

Scheme 1 describes the preparation of compounds of Formula I of the present invention. All of the final compounds of the present invention can be prepared by procedures described in these charts or by procedures analogous thereto, which procedures would be well known to one of ordinary skill in organic chemistry. All of the variables used in the scheme are as defined below or as in the claims.

General Procedure of Compounds Preparation of Formula 1 (Scheme 1)

7-Hydroxy-2-oxo-2H-chromene-3-carboxylic acid methyl ester (2) were obtained in the reaction of 2,4-dihydroxybenzaldehyde and dimethyl malonate in methanol with few drops of piperidine. Reaction performed at 60° C. in 48 h. Desired 2 isolated in good yield by filtration.

Butyl-, octyl-, and decyl-esters 3 were synthesized by treatment of 2 with chlorotrimethylsilane in appropriate alcohol (butanol, octanol, or decanol) as solvent followed by prolonged heating at 130° C. for 4-5 days. After cooling, the solvent was evaporated and precipitates washed with petroleum ether filtrated and dried to give pure esters 3.

Synthesis of 2-oxo-7-trifluoromethanesulfonyloxy-2H-chromene-3-carboxylic acid esters (4) performed in good yields in reaction of 2 and 3 with trifluoromethanesulfonyl anhydride in dry dichloromethane with excess of triethylamine at 0° C. The mixture was stirred for the 3 hours at rt and then cooled to 0° C. again. Ice water was added and the mixture was worked up with 1N HCl up to pH 2-3. Organic phase was separated, dried, filtered through SiO$_2$ and evaporated up to dryness giving a crystalline solid.

For triple bond introduction in position 7 modified Sonogashira protocol have been utilized. 7-(3-Hydroxy-3-methylbut-1-yn-1-yl)-2-oxo-2H-chromene-3-carboxylates (II) prepared by reaction of 4 with terminal acetylenes in the presence of a catalytic amount of tetrakis(triphenylphosphine)palladium(0) and/or palladium acetate, and copper iodide in dry DMF/triethylamine at 20° C. or slightly elevated temperature (up to 40° C.) under Ar atmosphere. After reaction completion, ethyl acetate and few drops of ammonia (aq.) were added followed by filtration through a silica gel pad. Then organic solution was washed with brine and dried. After solvent evaporation, desired products II were isolated by flash chromatography on silica gel.

Surprisingly, we have found that the treatment of ethynyl chromenes II with in situ prepared selenium(IV) bromide led to the formation of selenopheno[3,2-h]chromenes (I-1-I-10). Reaction performed by dissolving of selenium dioxide in concentrated hydrobromic acid followed by addition of ethynyl chromene II in dioxane; the mixture was stirred at rt for 24-48 hours. After the consumption of substrate II, the reaction mixture was made alkaline by aqueous $Na_2CO_3$ up to pH 8-9 and extracted with methylene chloride. The organic phase was washed with brine, dried, filtered, concentrated and the residue was purified by flash chromatography on silica gel. Appropriate carboxylic acids (I-11-I-15) prepared by simple hydrolysis of esters with an excess of sodium hydroxide in methanol-water. Typically, reaction mixture was left stirring for 5 days and then acidified with 2N HCl up to pH=2-3. The precipitate formed was filtered off, washed with cold acetonitrile and dried. Esters I-16-I-18, containing lipophilic substituents (e.g. octyl or cholesterol moiety) were prepared in two steps by treatment of carboxylic acids I-11-I-15 with excess of oxalic acid chloride in dichloromethane. Solvent was evaporated after 24 h of stirring and the crude product was dissolved in dry $CH_2Cl_2$. Meanwhile, in another flask corresponding alcohol and 0.5 equiv. of dimethylaminopyridine were dissolved in dry $CH_2Cl_2$ and excess of triethylamine. This flask was cooled in an ice bath and selenopheno[3,2-h]chromene-3-carboxylic acid chloride solution was added dropwise. After 24 h of stirring at room temperature. Esters I-16-I-18 were successfully isolated by flash chromatography on silica gel. Amides I-19-I-22 has been prepared in a similar manner using excess of secondary amines instead of alcohols.

Scheme 1. General procedure toward compounds of Formula I.

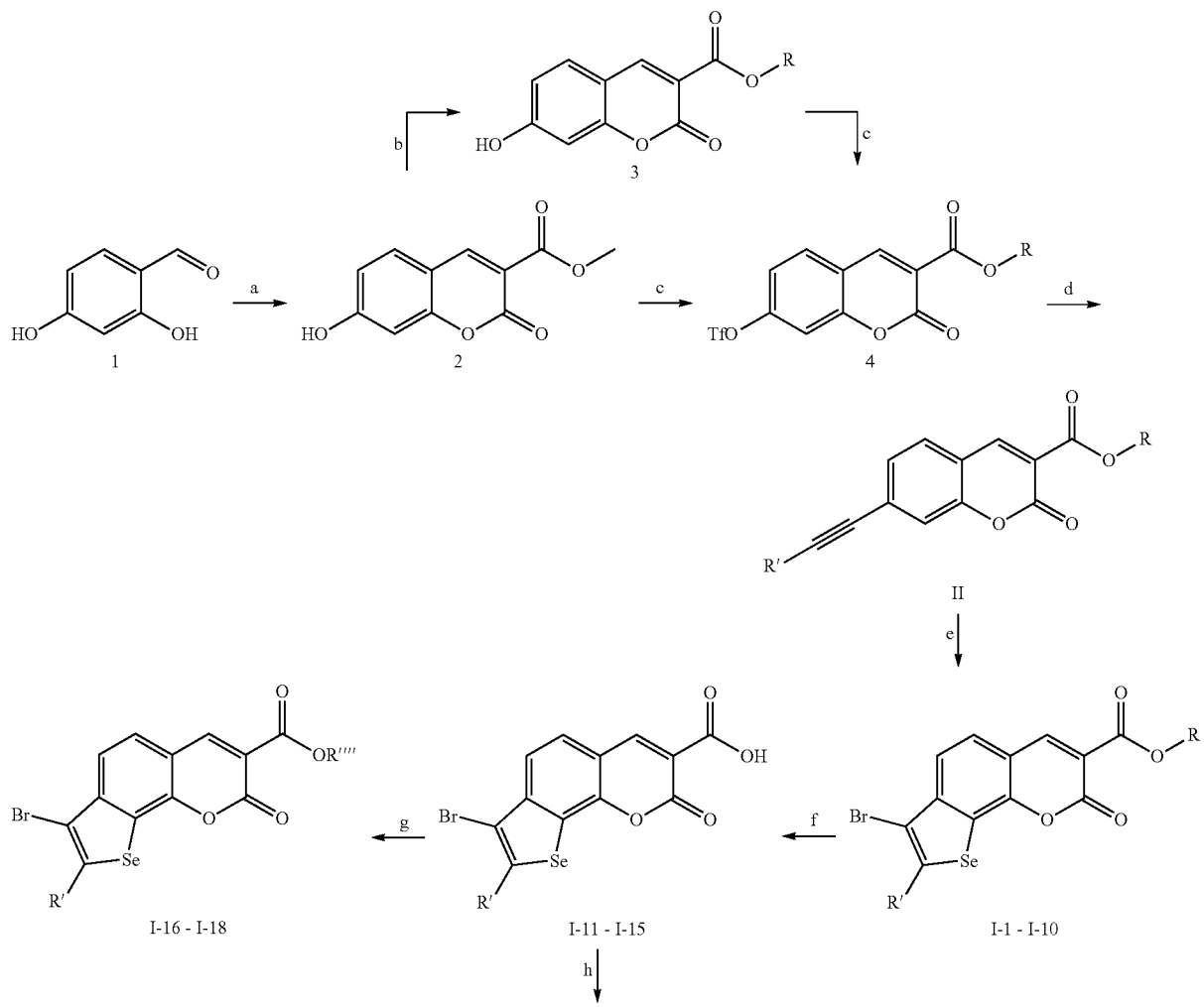

-continued

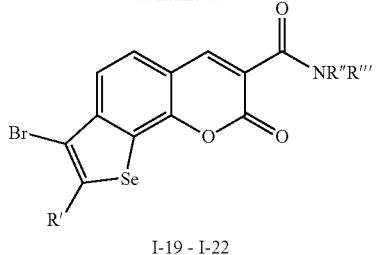

I-19 - I-22

Reaction conditions:
a: dimethyl malonate, methanol, piperdine, 48 h, 60° C.;
b: chlorotrimethylsilane, alcohol, 4-5 days, 130° C.;
c: trifluoromethanesulfonyl anhydride, triethylamine, dichloromethane, 0° C.;
d: terminal acetylene, tetrakis(triphenylphosphine)palladium(0) and/or palladium acetate, copper iodide, DMF/triethylamine, rt or 40° C., Ar;
e: selenium (IV) oxide, conc. hydrobromic acid, dioxane, rt;
f: sodium hydroxide, methanol/water, rt;
g: oxalyl chloride, alcohol, triethylamine, dichloromethane, 0° C.;
h: oxalyl chloride, amine, dichloromethane, 0° C..

EXAMPLES

Preparation of the disclosed compounds of the present invention is described in the following examples, which are intended as an illustration of and not a limitation upon the scope of the invention.

Hereinafter, "DMF" is defined as N,N-dimethylformamide, "DMAC" is defined as N,N-dimethylacetamide, "NMP" is defined as N-methylpyrrolidone, "DMSO" as dimethyl sulfoxide, "HCl" as hydrochloric acid, "aq. $NH_3$" as aqueous ammonia solution, "MeCN" as acetonitrile, "DIEA" as diisopropylethylamine, "EtOAc" as ethyl acetate, "rt" as room temperature.

Intermediate 2

Synthesis of 7-hydroxy-2-oxo-2H-chromene-3-carboxylic acid methyl ester (2). To the solution of 2,4-dihydroxybenzaldehyde (10 g, 0.072 mol) and dimethyl malonate (14 g, 0.108 mol) in 50 ml of dry methanol 6 drops of piperidine were added. Reaction mixture was stirred for 48 h at 60° C. Then, it was cooled to 0° C. and precipitates were filtered off, washed with ice-cold methanol and dried. Yield, 90%. $^1$H NMR: 3.79 (s, 3H), 4.08 (br s, 1H), 6.71 (d, 1H), 6.83 (dd, 1H), 7.74 (d, 1H), 8.68 (s, 1H).

Intermediates 3

Synthesis of 7-hydroxy-2-oxo-2H-chromene-3-carboxylic acid esters (3). Methyl 7-hydroxy-2-oxo-2H-chromene-3-carboxylate (3 g, 13.63 mmol) was suspended in appropriate alcohol (15 mL), and then 5 mL of $SiMe_3Cl$ was added. Then the reaction mixture was heated at 130° C. for 4-5 days. After cooling, the solvent was evaporated and precipitates washed with petroleum ether filtrated and dried to give pure ester.

7-Hydroxy-2-oxo-2H-chromene-3-carboxylic acid butyl ester (3a)

Yield, 64%. $^1$H-NMR: 0.92 (t, 3H), 1.35-1.47 (m, 2H), 1.60-1.70 (m, 2H), 4.21 (t, 2H), 6.72-6.73 (m, 1H), 6.82-6.86 (m, 1H), 7.75 (d, 1H), 8.65 (s, 1H).

7-Hydroxy-2-oxo-2H-chromene-3-carboxylic acid octyl ester (3b)

Yield, 68%. $^1$H-NMR: 0.87 (t, 3H), 1.26-1.42 (m, 8H), 1.71-1.78 (m, 2H), 4.31 (t, 2H), 6.86-6.88 (m, 2H), 7.43 (d, 1H), 8.48 (s, 1H).

7-Hydroxy-2-oxo-2H-chromene-3-carboxylic acid decyl ester (3c)

Yield, 63%. $^1$H-NMR: 0.88 (t, 3H), 1.23-1.38 (m, 14H), 1.61-1.70 (m, 2H), 4.20 (t, 2H), 6.73 (br s, 1H), 6.84 (dd, 1H), 7.76 (d, 1H), 8.65 (s, 1H).

Intermediates 4

Synthesis of 2-oxo-7-trifluoromethanesulfonyloxy-2H-chromene-3-carboxylic acid esters (4). Method presented for the preparation of 2-oxo-7-trifluoromethanesulfonyloxy-2H-chromene-3-carboxylic acid methyl ester (4a). Trifluoromethanesulfonyl anhydride (5.64 g, 20 mmol) was dropwise added to the solution of 7-hydroxy-2-oxo-2H-chromene-3-carboxylic acid methyl ester 2 (4 g, 18.2 mmol) and triethylamine (7.34 g, 72.7 mmol) in dry dichloromethane at 0° C. The mixture was stirred for the 3 hours (TLC control) and cooled to 0° C. Ice water was added and the mixture was worked up with 1N HCl up to pH 2-3. Organic phase was separated, dried over $MgSO_4$, filtered through $SiO_2$ and evaporated up to dryness giving a crystalline solid.

Yield: 63%; m.p. 156-158° C. GC-MS: 352 ($M^+$). $^1$H NMR ($CDCl_3$/HMDS) δ ppm: 3.97 (s, 3H, $OCH_3$), 7.28 (dd, 1H), 2.31 (d, 1H), 7.73 (d, 1H), 8.55 (s, 1H). $^{13}$C NMR ($CDCl_3$) δ ppm: 53.2, 110.4, 117.0, 117.7, 118.3, 119.0, 120.2, 131.2, 147.5, 152.5, 155.3, 155.7, 163.1.

2-Oxo-7-trifluoromethanesulfonyloxy-2H-chromene-3-carboxylic acid butyl ester (4b)

Yield: 44%; m.p. 122-123° C. $^1$H-NMR: 0.97 (t, 3H, J=6.9 Hz, $CH_3$), 1.42-1.52 (m, 2H, $CH_2$), 1.72-1.79 (m, 2H, $CH_2$), 4.36 (t, 2H, J=6.9 Hz, $CH_2$), 7.25-7.30 (m, 2H, 6-CH, 8-CH), 7.72 (d, 1H, J=8.6 Hz, 5-CH), 8.49 (s, 1H, 4-CH). $^{13}$C-NMR: 13.7, 19.1, 30.5, 66.2, 110.4, 117.0, 117.7, 118.1, 119.5, 131.1, 146.8, 152.4, 155.2, 155.7, 162.6.

2-Oxo-7-trifluoromethanesulfonyloxy-2H-chromene-3-carboxylic acid octyl ester (4c)

Yield: 96%. $^1$H NMR: 0.87 (t, 3H), 1.26-1.36 (m, 8H), 1.38-1.46 (m, 2H), 4.35 (t, 2H), 7.25-7.30 (m, 2H), 7.72 (d, 1H), 8.49 (s, 1H). $^{13}$C NMR: 14.1, 22.6, 25.8, 29.1, 29.2, 31.7, 66.5, 110.4, 117.0, 117.7, 118.1, 119.5, 120.2, 131.1, 146.8, 152.4, 155.2, 155.7, 162.5.

2-Oxo-7-trifluoromethanesulfonyloxy-2H-chromene-3-carboxylic acid decyl ester (4d)

Yield: 46%; m.p. 96-98° C. $^1$H NMR: 0.87 (t, 3H), 1.27-1.47 (m, 14H), 1.73-1.81 (m, 2H), 4.35 (t, 2H), 7.25-7.30 (m, 2H), 7.72 (d, 1H), 8.49 (s, 1H). $^{13}$C NMR: 14.0, 22.6, 25.8, 28.5, 29.1, 29.2, 29.4, 29.5, 31.8, 66.4, 110.3, 117.0, 117.7, 118.1, 119.5, 120.2, 131.1, 146.8, 152.3, 155.2, 155.6, 162.5.

Intermediates II

Synthesis of 7-(3-hydroxy-3-methylbut-1-yn-1-yl)-2-oxo-2H-chromene-3-carboxy-lates (II). Method presented for the preparation of methyl 7-(3-hydroxy-3-methylbut-1-yn-1-yl)-2-oxo-2H-chromene-3-carboxylate (IIa). The solution of 2-oxo-7-trifluoromethanesulfonyloxy-2H-chromene-3-carboxylic acid methyl ester (0.97 g, 2.76 mmol) and triethylamine (0.837 g, 8.28 mmol) in dry DMF (5 ml) was dropwise added under Ar atmosphere to the mixture of tetrakis(triphenylphosphine)palladium(0) (0.319 g, 0.276 mmol) and copper iodide (0.10 g, 0.552 mmol) in dry DMF (5 ml). Then 2-methylbut-3-yn-2-ol (0.46 g, 5.52 mmol) was added and the reaction mixture was left stirring at room temperature overnight. After reaction completion, ethyl acetate (150 ml) and few drops of ammonia (aq.) were added followed by filtration through a silica gel pad. Then organic solution was washed with brine (5×50 ml), dried over MgSO$_4$. After solvent evaporation desired product IIa was isolated by flash chromatography (silica gel, hexane/ethyl acetate as eluent). Yield: 65%, m.p. 168-170° C. GC-MS: 286 (M$^+$). $^1$H NMR (CDCl$_3$) δ ppm: 1.64 (s, 6H), 2.14 (s, 1H), 3.95 (s, 3H), 7.33 (dd, 1H), 7.34-7.36 (m, 1H), 7.52 (d, 1H), 8.51 (s, 1H). $^{13}$C NMR (CDCl$_3$) δ ppm: 31.2, 53.0, 65.6, 80.7, 99.1, 117.5, 117.9, 119.4, 128.0, 129.2, 148.3, 154.8, 156.4, 163.6.

Methyl 7-/(1-hydroxycyclopentyl)ethynyl/-2-oxo-2H-chromene-3-carboxylate (IIb)

Yield: 60%, m.p. 176-177° C. $^1$H-NMR: 1.77-1.92 (m, 4H), 2.04-2.07 (m, 4H), 2.09 (s, 1H), 3.94 (s, 3H), 7.31-7.33 (m, 2H), 7.51 (d, 1H, J=8.6 Hz), 8.50 (s, 1H). $^{13}$C-NMR: 23.5, 42.4, 52.9, 74.7, 81.6, 98.5, 117.4, 117.7, 119.3, 128.0, 129.2, 129.4, 148.3, 154.8, 156.3, 163.5.

Methyl 7-/(1-hydroxycyclohexyl)ethynyl/-2-oxo-2H-chromene-3-carboxylate (IIc)

Yield: 66%. M.p. 178-180° C. GC-MS: 326 (M$^+$). $^1$H NMR (CDCl$_3$/HMDS) δ ppm: 1.23-1.32 (m, 1H), 1.56-1.78 (m, 7H), 2.00-2.04 (m, 1H), 2.18 (s, 1H), 3.95 (s, 1H), 7.33 (s, 1H), 7.34 (d, 1H), 7.52 (d, 1H), 8.51 (s, 1H). $^{13}$C NMR (CDCl$_3$) δ ppm: 23.2, 25.1, 39.7, 52.9, 69.1, 82.8, 98.4, 117.5, 117.8, 119.4, 128.1, 129.3, 148.3, 154.9, 156.3, 163.6.

Methyl-7-/(1-methoxycyclohexyl)ethynyl/-2-oxo-2H-chromene-3-carboxylate (IId)

Yield: 57%, foam. $^1$HNMR: 1.30-1.31 (m, 1H), 1.52-1.60 (m, 3H), 1.61-1.74 (m, 4H), 1.96-2.00 (m, 2H), 3.42 (s, 3H), 3.95 (s, 3H), 7.34-7.38 (m, 2H), 7.53 (d, 1H), 8.51 (s, 1H). $^{13}$CNMR: 22.7, 25.3, 36.5, 50.9, 52.9, 74.3, 84.5, 96.2, 117.4, 117.8, 119.5, 128.1, 129.2, 129.4, 148.3, 154.9, 156.3, 163.5.

Butyl 7-/(1-hydroxycyclohexyl)ethynyl/-2-oxo-2H-chromene-3-carboxylate (IIe)

Yield: 61%, foam. $^1$H-NMR: 0.97 (t, 3H), 1.28-1.36 (m, 1H), 1.42-1.52 (m, 2H), 1.52-1.69 (m, 4H), 1.69-1.79 (m, 5H), 1.99-2.04 (m, 2H), 4.35 (t, 2H), 7.33-7.36 (m, 2H), 7.53 (d, 1H), 8.45 (s, 1H). $^{13}$CNMR: 13.7, 19.1, 23.2, 25.1, 30.6, 39.8, 65.9, 69.1, 82.9, 98.2, 117.6, 118.4, 119.4, 128.0, 129.13, 129.18, 147.6, 154.8, 156.3, 163.0.

Octyl 7-/(1-hydroxycyclohexyl)ethynyl/-2-oxo-2H-chromene-3-carboxylate (IIf)

Yield: 59%, foam. $^1$H-NMR: 0.86 (t, 3H), 1.26-1.35 (m, 9H), 1.38-1.46 (m, 2H, CH$_2$), 1.55-1.80 (m, 9H), 1.99-2.00 (m, 2H), 2.13 (s, 1H), 4.33 (t, 2H), 7.32-7.35 (m, 2H), 7.52 (d, 1H), 8.45 (s, 1H). $^{13}$CNMR: 14.1, 22.6, 25.1, 25.9, 28.5, 29.1, 29.2, 31.7, 39.7, 66.2, 69.1, 82.8, 98.2, 117.5, 118.4, 119.4, 128.0, 129.1, 129.2, 147.6, 154.8, 156.3, 163.0

Decyl 7-/(1-hydroxycyclohexyl)ethynyl/-2-oxo-2H-chromene-3-carboxylate (IIg)

Yield: 83%, foam. $^1$H-NMR: 0.87 (t, 3H), 1.26-1.45 (m, 14H), 1.56-1.80 (m, 9H), 2.00-2.04 (m, 2H), 2.06 (s, 1H), 4.34 (t, 2H), 7.33-7.36 (m, 2H), 7.52 (d, 1H), 8.45 (s, 1H). $^{13}$CNMR: 14.1, 22.6, 23.2, 25.1, 25.9, 28.5, 29.2, 29.3, 29.4, 29.5, 31.8, 39.7, 66.2, 69.1, 82.8, 98.2, 117.5, 118.3, 119.4, 128.0, 129.1, 129.2, 135.0, 147.6, 154.8, 156.3, 163.0.

Methyl 2-oxo-7-/3-(piperidin-1-yl)prop-1-yn-1-yl/-2H-chromene-3-carboxylate (IIh)

The mixture of tetrakis(triphenylphosphine)palladium(0) (98.5 mg, 0.085 mmol), palladium acetate (12.7 mg, 0.114 mmol), copper iodide (21.6 mg, 0.114 mmol) in dry DMF were stirred under Ar atmosphere at 40° C. for 20 min. The solution of 2-oxo-7-trifluoromethanesulfonyloxy-2H-chromene-3-carboxylic acid methyl ester (500 mg, 1.42 mmol) and triethylamine (0.43 g, 4.26 mmol) in dry DMF and the corresponding propargylamine (1.99 mmol) were subsequently added. The synthesis was carried out at 40° C. for 3 hours (TLC control). The reaction mixture was cooled to r.t., EtOAc was added. The mixture was washed with water and brine and filtered through a silica gel pad. Organic phase was separated, treated with 1N HCl and extracted with water. The water phase was washed with Et$_2$O, diluted with EtOAc and worked up with sat. Na$_2$CO$_3$ solution up to pH 8-9. Separated organic phase was dried over MgSO$_4$ and evaporated to dryness giving the pure product. Yield: 54%. m.p. 148-149° C. MS (EI) m/z: 326 [M+1]$^+$. $^1$H NMR (CDCl$_3$) δ ppm: 1.41-1.48 (m, 2H), 1.61-1.66 (m, 4H), 2.52-2.59 (m, 2H), 3.50 (s, 2H), 3.93 (s, 3H), 7.34 (d, 1H), 7.36 (s, 1H), 7.51 (d, 1H), 8.50 (s, 1H). $^{13}$C NMR (CDCl$_3$) δ ppm: 23.8, 25.9, 48.5, 52.9, 53.6, 83.6, 91.3, 117.3, 117.6, 119.46, 128.1, 129.2, 129.8, 148.3, 154.9, 156.4, 163.5.

Methyl 2-oxo-7-/3-(piperidin-1-yl)prop-1-yn-1-yl/-2H-chromene-3-carboxylate (IIi)

Yield: 60%. M.p. 146-148° C. MS (EI) m/z: 328 [M+1]$^+$. $^1$H NMR (CDCl$_3$) δ ppm: 2.65 (t, 4H), 3.56 (s, 2H), 3.78 (t, 4H), 3.96 (s, 3H), 7.34 (dd, 1H), 7.37 (d, 1H), 7.54 (d, 1H), 8.52 (s, 1H, 8-CH). $^{13}$C NMR (CDCl$_3$) δ ppm: 48.1, 52.5, 53.0, 66.8, 84.2, 90.0, 117.6, 117.9, 119.5, 128.2, 129.30, 148.3, 154.9, 156.3, 163.6.

Methyl 7-/3-(4-methylpiperazin-1-yl/prop-1-yn-1-yl)-2-oxo-2H-chromene-3-carboxylate (IIj)

Yield: 43%. M.p. 149-150° C. MS (EI) m/z: 341 [M+1]$^+$. $^1$H NMR (CDCl$_3$) δ ppm: 2.28 (s, 3H), 2.40-2.56 (m, 4H), 2.62-2.72 (m, 4H), 3.54 (s, 2H), 3.92 (s, 3H), 7.30-7.34 (m, 2H), 7.50 (d, 1H), 8.49 (s, 1H). $^{13}$C NMR (CDCl$_3$) δ ppm: 45.9, 47.6, 52.0, 52.9, 54.9, 84.0, 90.4, 117.4, 117.7, 119.4, 128.1, 129.2, 148.3, 154.8, 156.3, 163.5.

General Method for Preparation of selenopheno[3,2-h]chromenes (I)

To the solution of selenium dioxide (0.22 g, 2.0 mmol) in HBr (2 mL), ethynyl chromene II (1.0 mmol) in dioxane was added and the mixture was stirred at room temperature for 24-48 hours. After the consumption of substrate II (LC-MS), the reaction mixture was basified by aqueous Na$_2$CO$_3$ up to pH 8-9 and extracted with methylene chloride. The organic phase was washed with brine, dried over anhydrous Na$_2$SO$_4$, filtered, concentrated and the residue was purified by flash chromatography on silica gel using the mixture methylene chloride/ethyl acetate as eluent.

Example 1

Methyl 7-bromo-8-(2-hydroxypropan-2-yl)-2-oxo-2H-selenopheno[3,2-h]chromene-3-carboxylate (I-1)

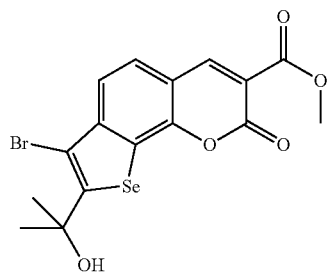 [SMILES: COC(=O)c1cc2ccc3c(Br)c(C(C)(C)O)[se]c3c2oc1=O]

Yield: 63%; m.p.>200° C. MS (EI) m/z: 445 [M+1]$^+$. 1H NMR (CDCl$_3$/HMDS) δ ppm: 1.88 (s, 6H), 3.99 (s, 3H), 7.64 (d, 1H), 7.79 (d, 1H), 8.81 (s, 1H). $^{13}$C NMR (CDCl$_3$) δ ppm: 28.7, 53.2, 75.1, 113.3, 115.4, 121.1, 122.2, 124.6, 126.1, 151.1, 162.1.

Example 2

Methyl 7-bromo-8-(cyclopent-1-en-1-yl)-2-oxo-2H-selenopheno[3,2-h]chromene-3-carboxylate (I-2)

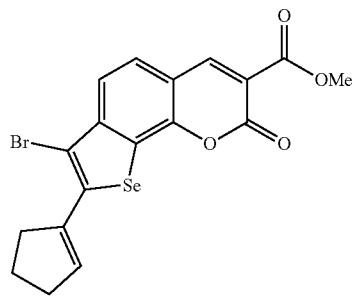 [SMILES: COC(=O)c1cc2ccc3c(Br)c(C4=CCCC4)[se]c3c2oc1=O]

Yield: 36%, m.p.=176-177° C. $^1$H NMR: 2.03-2.11 (m, 2H), 2.57-2.63 (m, 2H), 2.93-2.99 (m, 2H), 3.96 (s, 3H), 6.69-6.72 (m, 1H), 7.57 (d, 1H), 7.74 (d, 1H), 8.65 (s, 1H). $^{13}$CNMR: 23.4, 33.9, 36.9, 52.9, 105.9, 113.5, 116.2, 121.9, 124.3, 126.1, 136.5, 137.0, 144.8, 146.9, 149.7, 152.2, 156.2, 163.7.

Example 3

Methyl 7-bromo-8-(1-hydroxycyclohexyl)-2-oxo-2H-selenopheno[3,2-h]chromene-3-carboxylate (I-3

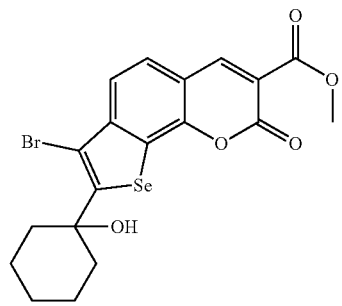 [SMILES: COC(=O)c1cc2ccc3c(Br)c(C4(O)CCCCC4)[se]c3c2oc1=O]

Yield: 66%. M.p.=260-265° C. MS (EI) m/z: 485 [M+1]$^+$. $^1$H NMR (CDCl$_3$) δ ppm: 1.37-1.46 (m, 1H), 1.69-1.88 (m, 7H), 2.52-2.61 (m, 2H), 2.74 (s, 1H), 3.97 (s, 3H), 7.59 (d, 1H), 7.76 (d, 1H), 8.68 (s, 1H). $^{13}$C NMR (CDCl$_3$) δ ppm: 21.6, 24.7, 34.9, 52.9, 75.9, 101.6, 113.1, 116.2, 121.6, 124.7, 125.8, 147.8, 149.9, 152.6, 156.4, 162.6, 163.8.

Example 4

Methyl 7-bromo-8-(1-methoxycyclohexyl)-2-oxo-2H-selenopheno[3,2-h]chromene-3-carboxylate (I-4)

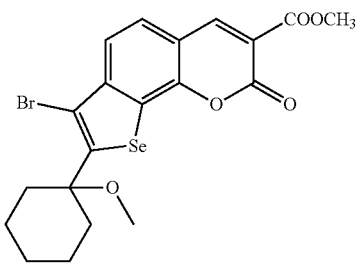 [SMILES: COC(=O)c1cc2ccc3c(Br)c(C4(OC)CCCCC4)[se]c3c2oc1=O]

Yield: 45%, m.p.=166-167° C. $^1$HNMR: 1.29-1.39 (m, 1H), 1.65-1.78 (m, 5H), 1.99-2.01 (m, 2H), 2.29-2.33 (m, 2H), 3.30 (s, 3H), 3.97 (s, 3H), 7.60 (d, 1H), 7.81 (d, 1H), 8.68 (s, 1H). $^{13}$CNMR: 21.7, 25.1, 34.7, 51.0, 52.9, 79.6, 104.6, 113.4, 116.4, 122.0, 124.8, 125.9, 147.3, 149.8, 152.4, 156.2, 157.9, 163.7. ESI-MS m/z: 498 [M].

Example 5

Butyl 7-bromo-8-(1-methoxycyclohexyl)-2-oxo-2H-selenopheno[3,2-h]chromene-3-carboxylate (I-5)

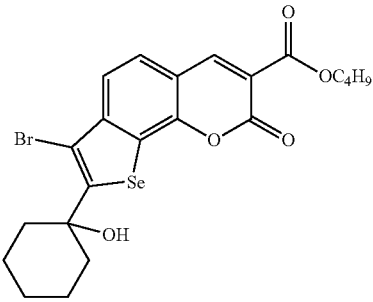

Yield: 61%, m.p.=202-204° C. $^1$H-NMR: 0.99 (t, 3H), 1.44-1.54 (m, 2H), 1.69-1.81 (m, 7H), 1.84-1.88 (m, 2H), 2.52-2.59 (m, 2H), 4.36 (t, 2H), 7.57 (d, 1H), 7.73 (d, 1H), 8.61 (s, 1H). $^{13}$CNMR: 13.7, 19.2, 21.6, 24.8, 30.6, 34.9, 65.8, 75.9, 101.5, 113.1, 116.7, 121.5, 124.6, 125.8, 147.7, 149.2, 152.5, 156.3, 162.5, 163.2. ESI-MS m/z: 541 [M].

Example 6

Octyl 7-bromo-8-(1-methoxycyclohexyl)-2-oxo-2H-selenopheno[3,2-h]chromene-3-carboxylate (I-6)

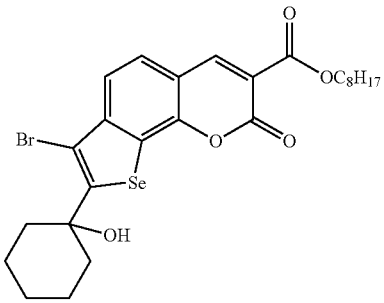

Yield: 33%, m.p.=189-190° C. $^1$H-NMR: 0.88 (t, 3H), 1.27-1.48 (m, 11H), 1.68-1.82 (m, 7H), 1.82-1.88 (m, 2H), 2.51-2.59 (m, 2H), 2.90 (s, 1H), 4.35 (t, 2H), 7.57 (d, 1H), 7.73 (d, 1H), 8.61 (s, 1H). $^{13}$C-NMR: 14.1, 21.6, 22.6, 24.8, 25.9, 28.6, 29.1, 29.2, 31.8, 34.9, 66.1, 75.9, 101.5, 113.1, 116.7, 121.5, ESI-MS m/z: 582 [M].

Example 7

Decyl 7-bromo-8-(1-methoxycyclohexyl)-2-oxo-2H-selenopheno[3,2-h]chromene-3-carboxylate (I-7)

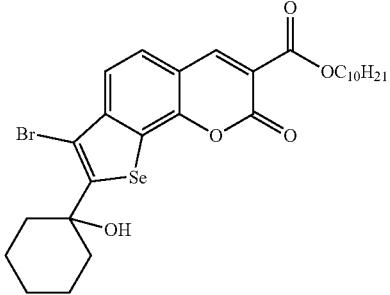

Yield: 28%, m.p.=175-176° C. $^1$H-NMR: 0.86-0.90 (m, 1H), 0.87 (t, 3H), 1.25-1.37 (m, 14H), 1.41-1.47 (m, 2H), 1.69-1.81 (m, 7H), 1.84-1.88 (m, 2H), 2.52-2.60 (m, 2H), 286 (s, 1H), 4.35 (t, 2H), 7.58 (d, 1H), 7.74 (d, 1H), 8.61 (s, 1H). $^{13}$C-NMR: 14.1, 21.6, 22.7, 24.8, 25.7, 25.9, 28.6, 29.3, 29.4, 29.5, 31.9, 121.5, 124.6, 125.8, 147.7, 149.3, 152.5, 156.4, 162.5, 163.2. ESI-MS m/z: 611 [M+1].

Example 8

Methyl 7-bromo-2-oxo-8-(piperidin-1-ylmethyl)-2H-selenopheno[3,2-h]chromene-3-carboxylate (I-8)

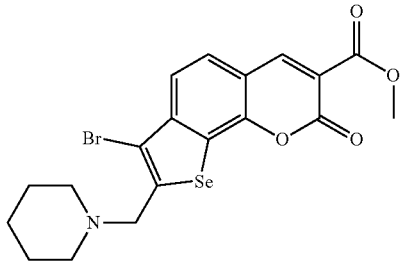 [SMILES: COC(=O)c1cc2ccc3c(Br)c(CN4CCCCC4)[se]c3c2oc1=O]

Yield: 65%, m.p.=125-130° C. MS (EI) m/z: 484 [M+1]$^+$. $^1$H NMR (CDCl$_3$/HMDS) δ ppm: 1.45-1.52 (m, 2H), 1.61-1.66 (m, 4H), 2.59-2.63 (m, 4H), 3.78 (s, 2H), 3.97 (s, 3H), 7.58 (d, 1H), 7.71 (d, 1H), 8.68 (s, 1H). $^{13}$C NMR (CDCl$_3$) δ ppm: 23.9, 26.1, 52.8, 55.3, 59.5, 104.8, 112.9, 116.0, 120.8, 125.8, 146.7, 149.9, 152.7, 155.2 156.3, 163.8.

Example 9

Methyl 7-bromo-8-(morpholinomethyl)-2-oxo-2H-selenopheno[3,2-h]chromene-3-carboxylate (I-9)

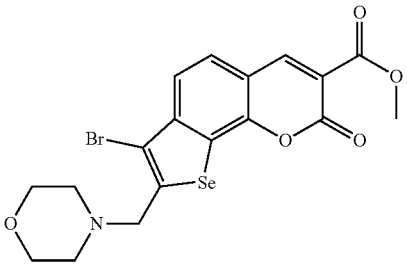 [SMILES: COC(=O)c1cc2ccc3c(Br)c(CN4CCOCC4)[se]c3c2oc1=O]

Yield: 48%. M.p. 150-155° C. MS (EI) m/z: 486 [M+1]$^+$. $^1$H NMR (CDCl$_3$/HMDS) δ ppm: 2.70 (t, 4H), 3.77 (t, 4H), 3.86 (s, 2H), 3.97 (s, 3H), 7.59 (dd, 1H), 7.73 (dd, 1H), 8.68 (d, 1H). $^{13}$C NMR (CDCl$_3$) δ ppm: 52.9, 54.1, 59.3, 67.0, 106.0, 113.2, 116.4, 121.1, 125.6, 126.0, 146.5, 149.9, 152.4, 152.7, 156.2, 163.7.

Example 10

Methyl 7-bromo-8-((4-methylpiperazin-1-yl)methyl)-2-oxo-2H-selenopheno[3,2-h]chromene-3-carboxylate (I-10)

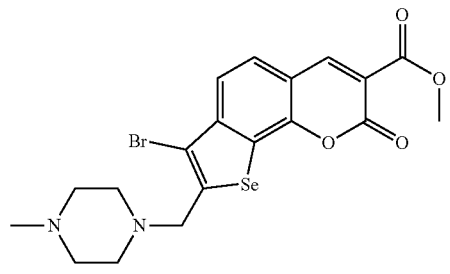

Yield: 34%, m.p.=115-118° C. (decomp.). MS (EI) m/z: 499 [M+1]$^+$. $^1$H NMR (CDCl$_3$/HMDS) δ ppm: 2.34 (s, 3H), 2.44-2.60 (m, 4H), 2.64-2.80 (m, 4H), 3.86 (s, 2H), 3.97 (s, 3H), 7.58 (d, 1H), 7.72 (d, 1H), 8.68 (s, 1H). $^{13}$C NMR (CDCl$_3$) δ ppm: 45.8, 52.8, 53.5, 55.0, 58.7, 105.4, 113.0, 116.1, 120.8, 125.5, 125.8, 146.5, 149.8, 152.6, 153.6, 156.1, 163.6.

General Method for Hydrolysis

Sodium hydroxide (276 mg, 6.9 mmol) as a saturated water solution was added to the solution of chromene (335 mg, 0.69 mmol) in 50 ml of methanol. Reaction mixture was left stirring for 5 days (TLC control) and then acidified with 2N HCl up to pH=2-3. The precipitate formed was filtered off, washed with cold acetonitrile and dried.

Example 11

7-Bromo-8-(1-hydroxycyclohexyl)-2-oxo-2H-selenopheno[3,2-h]chromene-3-carboxylic acid (I-11)

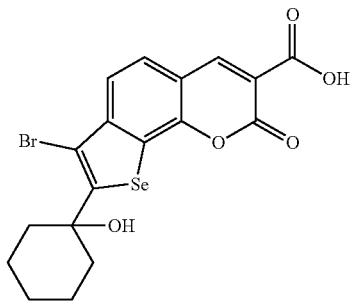 [SMILES: O=C(O)c1cc2ccc3c(Br)c(C4(O)CCCCC4)[se]c3c2oc1=O]

Yield: 98%. M.p.>200° C. $^1$H-NMR: 1.21-1.29 (m, 1H), 1.61-1.74 (m, 7H), 2.39-2.43 (m, 2H), 7.68 (d, 1H), 7.93 (d, 1H), 8.87 (s, 1H). ESI-MS m/z: 471 [M+1].

Example 12

7-Bromo-8-(1-methoxycyclohexyl)-2-oxo-2H-selenopheno[3,2-h]chromene-3-carboxylic acid (I-12)

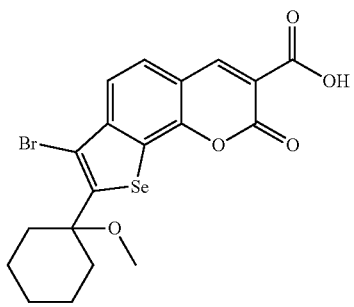 [SMILES: COC1(c2[se]c3c(ccc4cc(C(=O)O)c(=O)oc43)c2Br)CCCCC1]

Yield: 75%, m.p.>200° C. $^1$H-NMR: 1.30-1.41 (m, 1H), 1.67-1.81 (m, 5H), 2.05-2.12 (m, 2H), 2.28-2.32 (m, 2H), 3.34 (s, 3H), 7.73 (d, 1H), 7.93 (d, 1H), 9.04 (s, 1H). $^{13}$CNMR: 21.7, 25.1, 34.7, 51.0, 52.9, 79.6, 104.6, 113.4, 116.4, 122.0, 124.8, 125.9, 147.3, 149.8, 152.4, 156.2, 157.9, 163.7. ESI-MS m/z: 485 [M+1].

Example 13

7-Bromo-2-oxo-8-(piperidin-1-ylmethyl)-2H-selenopheno[3,2-h]chromene-3-carboxylic acid hydrochloride (I-13)

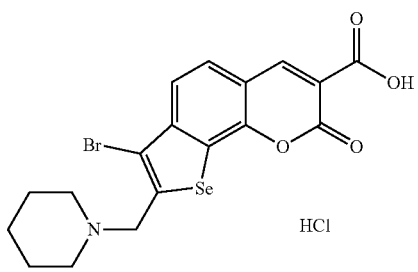 [SMILES: O=C(O)c1cc2ccc3c(Br)c(CN4CCCCC4)[se]c3c2oc1=O ; Cl]

Yield: 99%, m.p.=237-240° C. $^1$HNMR: 1.51-1.55 (m, 2H), 1.75-1.81 (m, 4H), 2.96-3.13 (m, 4H), 4.53 (br s, 1H), 7.76 (d, 1H), 7.98 (d, 1H), 8.88 (s, 1H). ESI-MS m/z: 470 [M+1].

Example 14

7-Bromo-2-oxo-8-(morpholin-1-ylmethyl)-2H-selenopheno[3,2-h]chromene-3-carboxylic acid hydrochloride (I-14)

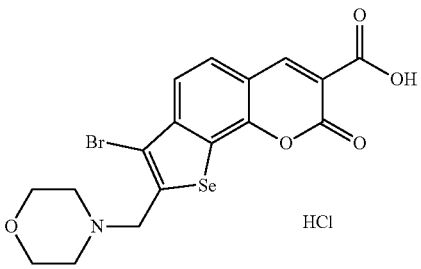 [SMILES: O=C(O)c1cc2ccc3c(Br)c(CN4CCOCC4)[se]c3c2oc1=O ; Cl]

Yield: 90%, m.p.>200° C. $^1$H-NMR: 3.03-3.38 (m, 4H), 3.82-3.98 (m, 4H), 4.72 (br s, 2H), 7.78 (d, 1H), 7.99 (d, 1H), 8.88 (s, 1H). ESI-MS m/z: 472 [M+1].

Example 15

7-Bromo-8-/(4-methylpiperazin-1-yl/methyl)-2-oxo-2H-selenopheno[3,2-h]chromene-3-carboxylic acid hydrochloride (I-15)

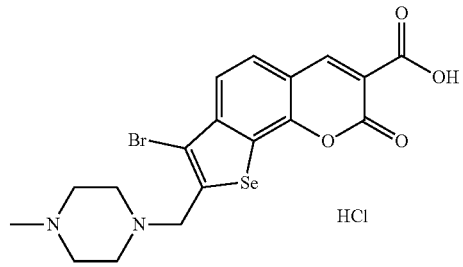 [SMILES: CN1CCN(Cc2[se]c3c(ccc4cc(C(=O)O)c(=O)oc43)c2Br)CC1 ; Cl]

Yield: 88%, m.p.>200° C. $^1$H-NMR: 2.66-2.79 (m, 4H), 2.78 (br s, 3H), 3.08-3.15 (m, 4H), 4.03 (s, 2H), 7.73 (d, 1H), 7.97 (d, 1H), 8.89 (s, 1H). ESI-MS m/z: 485 [M+1].

General Method for Synthesis of Amides and Esters from selenopheno[3,2-h]chromene-3-carboxylic acid 7-Bromo-2-oxo-2H-selenopheno[3,2-h]chromene-3-carboxylic acid (0.21 mmol) was suspended in dry $CH_2Cl_2$ (20 ml) and excess of oxalyl chloride (0.17 ml, 2 mmol) was added dropwise. Solvent was evaporated after 24 h of stirring and the crude product was dissolved in dry $CH_2Cl_2$ (20 ml). Meanwhile, in another flask secondary amine (10 equiv) or alcohol (0.61 mmol) and 0.5 equiv. DMAP (0.1 mmol, 13 mg) was dissolved in dry $CH_2Cl_2$ (10 ml). In the case of alcohol excess of $Et_3N$ (0.5 mL) was added to the mixture. This flask was cooled in an ice bath and selenopheno[3,2-h]chromene-3-carboxylic acid chloride solution was added dropwise. After 24 h of stirring at room temperature, amides or esters were isolated by flash chromatography on silica gel.

Example 16

Octyl 7-bromo-8-(cyclohex-1-en-1-yl)-2-oxo-2H-selenopheno[3,2-h]chromene-3-carboxylate (I-16)

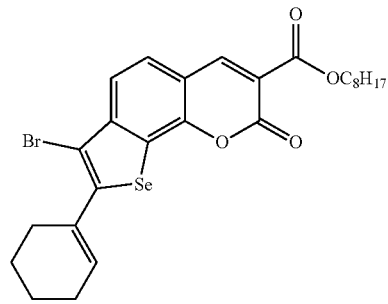

Yield: 31%, m.p.=145-147° C. $^1$H-NMR: 0.88 (t, 3H), 1.24-1.48 (m, 10H), 1.68-1.84 (m, 6H), 2.24-2.29 (m, 2H), 2.48-2.53 (m, 2H), 4.35 (t, 2H), 6.32-6.35 (m, 1H), 7.58 (d, 1H), 7.74 (d, 1H), 8.60 (s, 1H). $^{13}$C-NMR: 14.2, 21.5, 22.6, 22.7, 25.8, 25.9, 28.6, 29.1, 29.2, 29.9, 31.8, 66.1, 105.2, 113.4, 116.7, 121.9, 124.7, 126.0, 132.2, 133.5, 146.3, 149.1, 151.0, 152.2, 156.2, 163.1.

Example 17

(3S,8S,9S,10R,13R,14S,17R)-10,13-Dimethyl-17-((R)-6-methylheptan-2-yl)-2,3,4,7,8,9,10,11,12,13,14,15,16,17-tetradecahydro-1H-cyclopenta[a]phenanthren-3-yl-7-bromo-8-(cyclohex-1-en-1-yl)-2-oxo-2H-selenopheno[3,2-h]chromene-3-carboxylate (I-17)

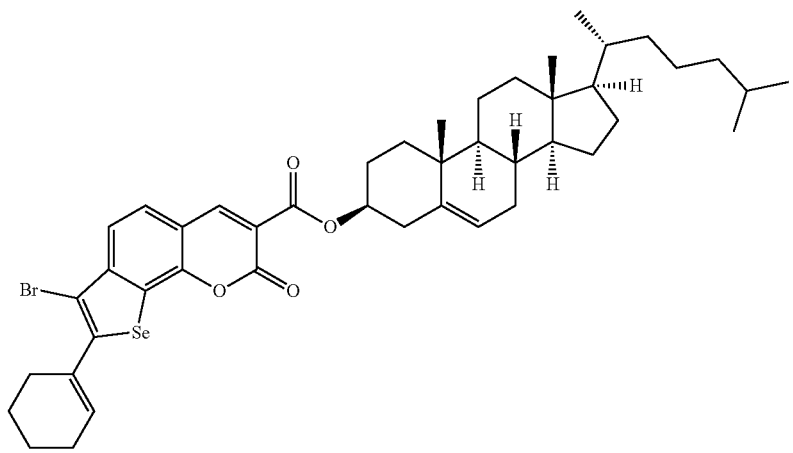

Yield: 26%, m.p.>200° C. $^1$H-NMR: 0.67 (s, 3H), 0.85 (dd, 6H), 0.90 (d, 3H), 0.94-1.57 (m, 20H), 1.67-2.02 (m, 13H), 2.33-2.37 (m, 2H), 2.46-2.51 (m, 4H), 4.81-4.90 (m, 1H, CH), 5.39-5.41 (m, 1H), 6.30-6.33 (m, 1H), 7.56 (d, 1H), 7.73 (d, 1H), 8.57 (s, 1H). $^{13}$C-NMR: 11.8, 18.7, 19.3, 21.0, 21.5, 22.5, 22.7, 22.8, 23.8, 24.3, 25.8, 27.8, 28.0, 28.2, 29.9, 31.8, 31.9, 35.8, 36.2, 36.6, 36.9, 38.0, 39.5, 39.7, 42.3, 49.9, 56.1, 56.6, 75.7, 105.2, 113.4, 116.9, 121.9, 122.9, 124.7, 125.9, 132.3, 133.5, 139.4, 146.2, 148.8, 150.9, 152.2, 156.2, 162.2.

Example 18

(3S,8S,9S,10R,13R,14S,17R)-10,13-Dimethyl-17-((R)-6-methylheptan-2-yl)-2,3,4,7,8,9,10,11,12,13,14,15,16,17-tetradecahydro-1H-cyclopenta[a]phenanthren-3-yl 7-bromo-8-(1-methoxycyclohexyl)-2-oxo-2H-selenopheno[3,2-h]chromene-3-carboxylate (I-18)

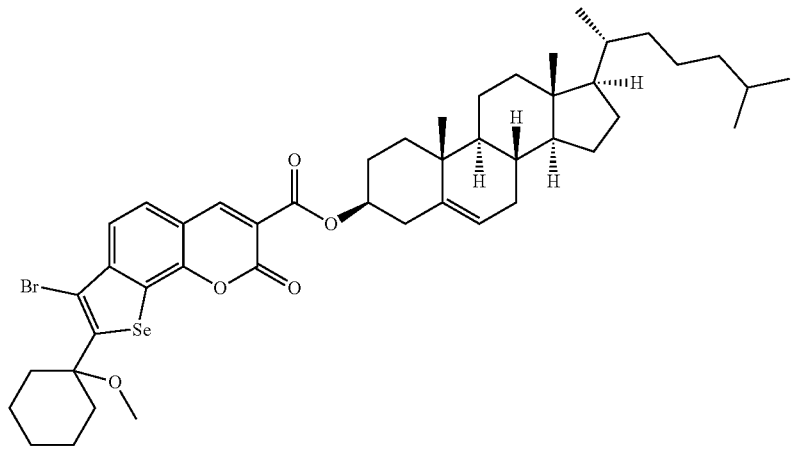

Yield: 24%, m.p.>200° C. $^1$H-NMR: 0.68 (s, 3H), 0.86 (dd, 6H), 0.92 (d, 3H), 0.94-1.04 (m, 3H), 1.06 (s, 3H, CH$_3$), 1.11-1.38 (m, 12H), 1.44-1.59 (m, 6H), 1.67-1.86 (m, 7H), 1.91-2.06 (m, 6H), 2.31-2.34 (m, 2H), 2.48-2.50 (m, 2H), 3.30 (s, 3H), 4.84-4.92 (m, 1H), 5.41-5.43 (m, 1H), 7.60 (d, 1H), 7.81 (d, 1H), 8.60 (s, 1H). $^{13}$C-NMR: 11.8, 18.7, 19.3, 21.0, 21.6, 22.5, 22.8, 23.8, 24.3, 25.1, 27.7, 28.0, 28.2, 31.8, 31.9, 34.7, 35.8, 36.1, 36.6, 36.9, 38.0, 39.5, 39.7, 42.3, 49.9, 51.0, 56.1, 56.6, 75.7, 79.5, 104.6, 113.4, 117.2, 121.9, 122.9, 124.8, 125.8, 139.4, 147.1, 148.8, 152.2, 156.2, 157.5, 162.2.

Example 19

7-Bromo-8-(cyclohex-1-en-1-yl)-3-(piperidine-1-carbonyl)-2H-selenopheno[3,2-h]chromen-2-one (I-19)

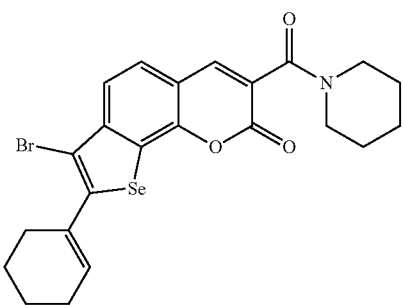 [SMILES: O=C(c1cc2ccc3c(Br)c(C4=CCCCC4)[se]c3c2oc1=O)N1CCCCC1]

Yield: 29%, foam. $^1$H-NMR: 1.62-1.74 (m, 8H), 1.78-1.84 (m, 2H), 2.24-2.28 (m, 2H), 2.48-2.53 (m, 2H), 3.34-3.37 (m, 2H), 3.70-3.74 (m, 2H), 6.30-6.33 (m, 1H), 7.51 (d, 1H), 7.73 (d, 1H), 7.97 (s, 1H). $^{13}$C-NMR: 21.5, 22.7, 24.4, 25.4, 25.8, 26.2, 29.9, 43.1, 48.4, 105.1, 114.0, 121.9, 124.5, 124.8, 125.2, 132.2, 133.3, 143.1, 144.9, 149.5, 150.9, 157.5, 163.2.

Example 20

7-Bromo-8-(cyclohex-1-en-1-yl)-3-(morpholine-1-carbonyl)-2H-selenopheno[3,2-h]chromen-2-one (I-20)

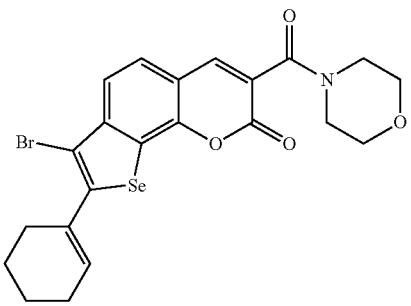 [SMILES: O=C(c1cc2ccc3c(Br)c(C4=CCCCC4)[se]c3c2oc1=O)N1CCOCC1]

Yield: 34%, m.p.=195-196° C. $^1$H-NMR: 1.69-1.75 (m, 2H), 1.79-1.85 (m, 2H), 2.24-2.30 (m, 2H), 2.49-2.54 (m, 2H), 3.44 (t, 2H), 3.74 (t, 2H), 3.80-3.82 (m, 4H), 6.32-6.35 (m, 1H), 7.54 (d, 1H), 7.77 (d, 1H), 8.07 (s, 1H). $^{13}$C-NMR: 21.5, 22.7, 25.8, 29.9, 42.7, 47.7, 66.7, 105.1, 113.9, 122.1, 123.3, 124.8, 125.3, 132.2, 133.4, 144.7, 145.4, 149.9, 151.1, 157.5, 163.6.

Example 21

7-Bromo-8-(cyclohex-1-en-1-yl)-N,N-bis(2-methoxyethyl)-2-oxo-2H-selenopheno[3,2-h]chromene-3-carboxamide (I-21)

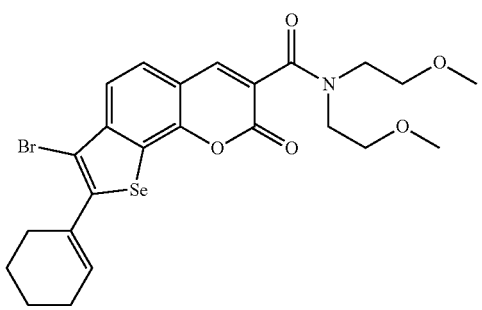 [SMILES: COCCN(CCOC)C(=O)c1cc2ccc3c(Br)c(C4=CCCCC4)[se]c3c2oc1=O]

Yield: 27%, foam. $^1$H-NMR: 1.67-1.83 (m, 4H), 2.22-2.28 (m, 2H), 2.48-2.53 (m, 2H), 3.28 (s, 3H), 3.39 (s, 3H), 3.49-3.58 (m, 4H), 3.66-3.77 Se (m, 4H), 6.29-6.33 (m, 1H), 7.49 (d, 1H), 7.72 (d, 1H), 7.92 (s, 1H). $^1$C-NMR: 21.5, 22.7, 25.8, 29.9, 45.7, 49.8, 58.8, 58.9, 70.3, 70.7, 105.0, 113.9, 121.9, 124.3, 124.8, 125.1, 132.2, 133.2, 143.1, 144.9, 149.3, 150.8, 157.7, 165.6.

Example 22

7-Bromo-8-(1-methoxycyclohexyl)-3-(morpholine-4-carbonyl)-2H-selenopheno[3,2-h]chromen-2-one (I-22)

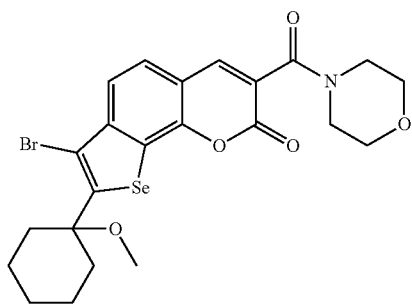 [SMILES: COC1(c2[se]c3c(ccc4cc(C(=O)N5CCOCC5)c(=O)oc43)c2Br)CCCCC1]

Yield: 40%, foam. $^1$H-NMR: 1.30-1.39 (m, 1H), 1.64-1.77 (m, 5H), 1.99-2.07 (m, 2H), 2.29-2.32 (m, 2H), 3.30 (s, 3H), 3.42 (t, 2H), 3.72 (t, 4H), 3.79 (br s, 4H), 7.53 (d, 1H), 7.80 (d, 1H), 8.06 (s, 1H). $^{13}$C-NMR: 21.7, 25.1, 34.7, 42.6, 47.7, 51.0, 66.5, 66.6, 79.5, 104.5, 113.8, 122.0, 123.5, 124.8, 125.1, 144.6, 146.2, 151.1, 156.5, 157.4, 163.5. ESI-MS m/z: 554 [M+1].

Cytotoxicity and anticancer activity against primary tumor and metastasis of synthesized compounds of Formula 1 were tested on cell lines and on animal models.

1. Antiproliferative Activity In Vitro

Anticancer activity of selenopheno[h]chromenes was tested in vitro using cytotoxicity assay. Thus, monolayer tumor cell lines MDA-MB-435s (human melanoma), MCF-7 (human breast adenocarcinoma, estrogen-positive), MES-SA (human uterus sarcoma), HT-1080 (human fibrosarcoma), A549 (human lung carcinoma), SH-SY5Y (human neuroblastoma), CCL-8 (mouse sarcoma), MG-22A (mouse hepatoma), and HepG2 (human hepatocellular carcinoma) were cultured in standard medium DMEM (Dulbecco's modified Eagle's medium) ("Sigma") supplemented with 10% fetal bovine serum ("Sigma"). About $2\text{-}9 \cdot 10^4$ cells/mL (depending on line nature) were placed in 96-well plates immediately after compounds were added to the wells. Untreated cells were used as a control. The plates were incubated for 72 h, 37° C., 5% $CO_2$. The number of surviving cells was determined using 3-(4,5-dimethylthiazol-2-yl)-2,5-diphenyltetrazolinium bromide (MTT). MTT-test: after incubating culture medium was removed and 200 μL fresh medium with 10 mM HEPES was added in each well of the plate, than 20 μL MTT (2 mg/mL in HBSS) was added. After incubation (3 hr, 37° C., 5% $CO_2$), the medium with MTT was removed and 200 μL DMSO were added at once to each sample. The samples were tested at 540 nm on Anthos HT II photometer.

In parallel, the borderline concentration relevant to the highest tolerated dose has been determined for each compound using the NIH 3T3 (mouse embryo fibroblasts) cell line and the basal cytotoxicity obtained has then been used to predict the starting doses for in vivo acute oral $LD_{50}$ values in rodents.

Basal Cytotoxicity Test:

the Neutral Red Uptake (NRU) assay was performed according to the standard protocol of Stokes modified by the NICEATM-ECVAM validation study. The NRU cytotoxicity assay procedure is based on the ability of viable cells to incorporate and bind Neutral Red, a supravitally dye. Balb/c 3T3 (Mouse Swiss Albino embryo fibroblast) cells (9000 cells/well) were placed into 96-well plates for 24 h in Dulbecco's modified Eagle's (DMEM) medium containing 5% fetal bovine serum. The cells were then exposed to the test compounds over a range of eight concentrations (1000, 316, 100, 31, 10, 3, 1 μg/ml) for 24 h. Untreated cells were used as a control. After 24 h, the medium was removed from all plates. Then, 250 μL of Neutral Red solution were added (0.05 mg/mL NR in DMEM 24 h pre-incubated at 37° C. and then filtered before use through 0.22-μm syringe filter). Plates were incubated for 3 h and then cells were washed three times with PBS. The dye within viable cells was released by extraction with a mixture of acetic acid, ethanol and water (1:50:49). Absorbance of Neutral Red was measured using a spectrophotometer multiplate reader (TECAN, Infinite M1000) at 540 nm. The percentage of living cells was calculated using the formula: OD (treated cells)*100/OD (control cells). The $IC_{50}$ values were calculated using the programme Graph Pad Prism® 3.0.

Estimation of $LD_{50}$ from $IC_{50}$ Values:

Data from the in vitro tests were used for estimating the starting dose for acute oral systemic toxicity tests in rodents. The in vivo starting dose is an estimated $LD_{50}$ value calculated by inserting the in vitro $IC_{50}$ value into a regression formula: log $LD_{50}$ (mM/kg)=0.439 log $IC_{50}$ (mM)+0.621. The value is recalculated to mg/kg and compounds are evaluated in accordance with four toxicity categories: category 1: $LD_{50} \leq 5$ mg/kg (highly toxic); category 2: $5 < LD_{50} \leq 50$ mg/kg (moderately toxic); category 3: $50 < LD_{50} \leq 300$ mg/kg (slightly toxic); category 4: $300 < LD_{50} \leq 2\,000$ mg/kg (practically non-toxic).

Acute Toxicity Determination.

Acute p.o. toxicity ($LD_{50}$) was estimated by the Up-and-Down Procedure according to the OECD Test Guideline 425 [OECD (2001) Guideline for testing of chemicals OECD 425, acute oral toxicity—Up-and-Down Procedure, Paris, p. 1-26]. Animals were observed daily for clinical signs or mortality over a period of two weeks following the treatment. Compounds were dissolved in DMSO and then in PBS Acute toxicity in vivo has been determined for I-10 and I-11 on 6 weeks old male ICR mice. Surprisingly, according to our data acute toxicity for I-10 is 891 mg/kg and I-11—more than 2000 mg/kg after p.o. administration in mice.

TABLE 1

In vitro cytotoxicity of selenopheno[h]chromenes on monolayer tumor cell lines: MDA-MB-435s (human melanoma), MCF-7 (human breast adenocarcinoma, estrogen-positive), MES-SA (human uterus sarcoma), HT-1080 (human fibrosarcoma), A549 (human lung carcinoma), SH-SY5Y (human neuroblastoma), CCL-8 (mouse sarcoma), 3T3 (mouse embryo fibroblasts), MG-22A (mouse hepatoma), HepG2 (human hepatocellular carcinoma).

| | Cytotoxicity $IC_{50}$, µM | | | | | | | | | Basal cytotoxicity Estimated* $LD_{50}$ | |
|---|---|---|---|---|---|---|---|---|---|---|---|
| Nr. | MDA-MB-435s | MCF-7 | MES-SA | HT-1080 | A549 | SHSY5Y | CCL-8 | 3T3 | MG-22A | HepG2 | µM/kg | mg/kg |
| I-1 | 95 ± 8 | 221 ± 13 | 95 ± 9 | 225 ± 11 | 196 ± 9 | 32 ± 3 | >225 | 225 ± 11 | — | — | >6000 | >2665 |
| I-2 | 142 ± 12 | 281 ± 12 | 155 ± 3 | 110 ± 12 | 122 ± 8 | — | 82 ± 8 | >235 | >235 | 197 ± 24 | 500 | 194 |
| I-3 | 64 ± 6 | 29 ± 2 | 66 ± 3 | 27 ± 1 | 19 ± 2 | 19 ± 3 | 186 ± 9 | 207 ± 9 | 33 ± 6 | — | >5600 | >2712 |
| I-4 | 103 ± 4 | 46 ± 14 | 201 ± 5 | 52 ± 5 | >201 | — | 95 ± 2 | 198 ± 2 | 446 ± 6 | 103 ± 5 | 1100 | 548 |
| I-5 | — | >190 | >190 | — | >190 | — | >190 | — | — | 51 ± 5 | >3800 | >2000 |
| I-6 | >171 | 66 ± 10 | >171 | >171 | >171 | 50 ± 1 | >171 | — | — | 89 ± 5 | >3400 | >2000 |
| I-7 | 152 ± 9 | 48 ± 13 | >164 | >164 | >164 | — | 81 ± 2 | >164 | >164 | 151 ± 6 | >3300 | >2000 |
| I-8 | >192 | 165 ± 5 | — | >192 | 115 ± 8 | >192 | — | 54 ± 3 | 46 ± 3 | 181 ± 9 | >3900 | >2000 |
| I-9 | 67 ± 8 | 81 ± 6 | 54 ± 7 | 86 ± 6 | 86 ± 6 | 46 ± 9 | 84 ± 6 | 56 ± 3 | 48 ± 3 | 90 ± 6 | 2400 | 1252 |
| I-10 | >187 | 150 ± 9 | >187 | 170 ± 9 | 187 ± 10 | — | 94 ± 7 | 86 ± 5 | 64 ± 5 | 187 ± 10 | 4300 | 2299 |
| I-11 | 208 ± 13 | 213 ± 6 | 206 ± 10 | 77 ± 5 | >213 | — | 149 ± 9 | >213 | — | >213 | >5800 | >2727 |
| I-12 | 127 ± 12 | 141 ± 10 | >206 | 51 ± 2 | 61 ± 1 | 193 ± 2 | 134 ± 6 | 213 ± 7 | >206 | 97 ± 7 | 300 | 134 |
| I-13 | 182 ± 11 | 119 ± 2 | 103 ± 9 | 197 ± 3 | 129 ± 6 | >197 | — | 197 ± 8 | 49 ± 6 | >197 | 4300 | 2175 |
| I-14 | 156 ± 9 | 95 ± 9 | 65 ± 6 | 100 ± 6 | 51 ± 8 | 35 ± 9 | 79 ± 9 | 43 ± 2 | 59 ± 2 | 106 ± 9 | 2600 | 1320 |
| I-15 | — | >192 | — | >192 | >192 | >192 | — | 192 ± 7 | 186 ± 7 | >192 | 3200 | 1666 |
| I-16 | — | — | — | — | — | — | — | >177 | — | >177 | 500 | 876 |
| I-17 | — | — | — | — | — | — | — | — | — | — | 3000 | 2454 |
| I-18 | >117 | — | — | — | — | — | >117 | — | >117 | — | 3700 | 3192 |
| I-19 | 51 ± 8 | 125 ± 8 | 105 ± 4 | 50 ± 5 | 100 ± 3 | — | >193 | 161 ± 23 | 41 ± 2 | 103 ± 15 | 1000 | 500 |
| I-20 | 13 ± 1 | 81 ± 7 | 61 ± 4 | 92 ± 12 | 38 ± 5 | — | 126 ± 4 | >192 | 117 ± 7 | 63 ± 6 | 3000 | 1605 |
| I-21 | 76 ± 4 | 92 ± 12 | 73 ± 3 | 51 ± 1 | 61 ± 6 | 139 ± 6 | 100 ± 8 | 131 ± 7 | 46 ± 6 | 51 ± 7 | 700 | 384 |
| I-22 | 43 ± 3 | 18 ± 2 | 41 ± 2 | 38 ± 2 | 43 ± 4 | 98 ± 3 | 39 ± 3 | 47 ± 4 | 37 ± 1 | 47 ± 2 | 300 | 195 |

*Estimated acute oral $LD_{50}$ was calculated based on $IC_{50}$ (mM) value from 3T3 NRU assay using the regression formula: log $LD_{50}$ (mM/kg) = 0.439 log $IC_{50}$ (mM) + 0.621
"—" - no effect (pH 7.4; DMSO final concentration <1%). The test substance was administered in a single dose p.o. to mice. Animals were observed daily for clinical signs or mortality over a period of two weeks following the treatment.

The results of cell culture-based studies are summarized in Table 1.

In general, tested compounds showed medium or low cytotoxicity against malignant tumor cells. Notably, all derivatives are low toxic to normal NIH 3T3 cells according to basal cytotoxicity test ($LD_{50}$>1252 mg/kg) what is very surprisingly for Se-containing compounds. Derivative I-1 is able to suppress SHSY5Y cells growth ($IC_{50}$=32 µM). Also hydroxycyclohexyl-selenopheno[h]chromene 1-3 exhibits moderate antiproliferative activity ($IC_{50}$ up to 19 µM on A549 and SHSY5Y cancer cell lines) and simultaneously it is low toxic to normal mouse embryo fibroblasts NIH 3T3 (estimated basal toxicity $LD_{50}$ is equal to 2712 mg/kg). Hydrolysis of ester group (compound I-11) led to complete loss of cytotoxicity. Morpholinomethylselenopheno[h]chromene 1-9 possess medium cytotoxicity, however, this compound is the most toxic among studied chromenes against normal NIH 3T3 cells. Corresponding carboxylic acid I-14 remained cytotoxicity on cancer cell lines and substantial basal toxicity ($LD_{50}$=1320 mg/kg). N-methyl-piperazinomethyl substituted selenopheno[h]chromenes I-10 and I-15 are low toxic to the cancer cell lines, which demonstrated higher input of structural features on the cytotoxic activity of tested compounds rather than presence of selenium or coumarin backbone in the molecule.

2. Evaluation of Anticancer Activity In Vivo

Mouse Non-Metastatic Cancer Models.
Mice.

Six-week-old female ICR and BALB/c mice were purchased from the University of Tartu Laboratory Animal Centre (Estonia). The mice were housed five to a cage, and under standard conditions (21-23° C., 12 h light: dark cycle), fed ad libitum (R3 diet, Lactamin AB, Kimstad, Sweden) and observed daily. The experimental procedures involving experimental animals were carried out in accordance with the guidelines of the European Community, local laws and policies, and were approved by the Latvian Animal Protection Ethical Committee, the Food and Veterinary Service, Riga, Latvia.

Cell Lines:

In vivo studies were performed utilizing the mouse sarcoma CCRF-S180 II (CCL-8) and Lewis lung carcinoma (LLC) cell line. All cell lines were purchased from ATCC. The cells were grown in Dulbecco's modified Eagle's medium (Sigma) supplemented with 10% fetal calf serum (Sigma).

Testing of Anticancer Activity of Disclosed Compounds were Performed In Vivo in mouse non-metastatic cancer models.

ICR mice were subcutaneously inoculated in the back with 5×10⁶ CCL-8 cells and BALB/c mice were inoculated with 1×10⁶ LLC (Lewis Lung Carcinoma) cells, which were suspended in 0.1 mL of PBS on day zero of the study. The compounds dissolved in DMSO and then in 0.1 mL water (DMSO final concentration 1%) were injected s.c. Mice in the untreated group were similarly given doses of 0.1 mL of water with DMSO. Tumor volume (tumor volume V=47tab2/3, a is maximal and b the minimal tumor diameter) was recorded twice per week. The mice were examined every other day for diseases including appearance, weight and behavior. The mice were sacrificed at day 16 of the experiment by decapitation after ketamine/xylazine anesthesia.

Results are presented in Table 4. Surprisingly, after a course of injections of I-9-I-11 in total dose 45 mg/kg a volume of sarcoma CCL-8 tumor decreased by 38-58%. Additionally, derivative I-10 was able to suppress LLC primary tumor growth by 34%. It should be noted, that no side effects were detected on all animal groups.

TABLE 4

Anticancer activity in vivo caused by selenopheno[h]chromenes (inhibition, %)

| Conditions | I-9 | I-10 | I-11 |
|---|---|---|---|
| CCL-8. Administration: s.c. according to the following scheme: Day 1, 2, 3, 4, 7, 8, 9, 10, 11; dose 5 mg/kg. Total dose 45 mg/kg. | 38** | 42** | 58* |
| Lewis Lung Carcinoma. Administration: s.c. according to the following scheme: Day 1, 2, 3, 4, 7, 8, 9, 10, 11; dose 20 mg/kg. Total dose 180 mg/kg. |  | 34* |  |

*$p < 0.05$;
**$p < 0.15$ compared with control by Student's two-tailed t test

3. Evaluation of Antimetastatic Activity In Vivo

In Vivo Model of Haematogenous Metastatic Dissemination. There are various in vivo experimental models for the study of growth and metastasis of different tumors after transplantation. The injection site and the particular tumor tropism selected cell line is mainly determined by the primary and secondary metastases and the growth of their location.

Pulmonary metastases model is widely used to assess the treatment of many tumor models, including B16 melanoma and breast carcinoma 4T1. Melanoma of the skin can be cured by surgical removal of the early stages, but the high metastatic potential and resistance to chemotherapy leads to a high level of recurrence. 5-year survival rate in the diagnosis of metastasis in 2013 was only 15%, and only slightly improved from 12% in the past decade. (Cancer Facts and FIGS. 2013. American Cancer Society. Atlanta, Ga., USA, 2013). One of the most aggressive forms of skin cancer melanoma B16-F10 was chosen for intravenous administration in the tail vein formed lung metastases (Poste et al, Cancer Res., 1980, 40, 1636-1644).

Melanoma Model of Lung Metastasis.

C57BL/6 mice were injected with 100,000 B16-F10 melanoma cells into the mice via the tail vein and treatment started 24 hr later with subcutaneous injections (s.c.) of compounds administered according to the following scheme: 1, 7, 8, 9, 10, 11 and 14th days in dose 20 mg/kg. Mice in the control group were similarly given doses of 0.1 mL of water with DMSO (DMSO final concentration <1%). Twenty-one days later, all mice were anesthetized with ketamine/xylazine and euthanized, the mice were sacrificed and the black melanoma nodules on the lungs were measured. In each experiment, mice were weighed twice weekly.

Based on data received from performed experiments (FIG. 1) using B16-F10 melanoma lung metastasis model we confirmed unexpected and extraordinary result that selenopheno[h]chromene I-10 inhibits melanoma metastasis in lung by 74% (Administration: s.c. according to the following scheme: Day1, 7, 8, 9, 10, 11, 14; Total dose 140 mg/kg dose). When analyzing the impact of I-10 on each individual mouse in the group of six animals, we observed that melanoma metastasis in five animals was completely prevented, but in one—did not. Use of compound I-11 under the same experimental conditions led us to conclude that this compound almost completely prevents melanoma metastasis in lung (96%). Moreover, in four animals out of six metastases not observed at all.

Evaluation of Antimetastatic Activity

Syngeneic mice model of breast carcinoma 4T1 (American Type Culture Collection (ATCC) catalogue no CRL-2539, 2004) is an excellent model which mimics the clinical parameters of human breast cancer. Using different methods of administration these cells to mice the tumor metastasis are formed in various organs and uses different pathways for spreading.

Thus, implantation of 4T1 cells in orthotropic mouse mammary gland induce development of metastasis in lung, lymph nodes, liver, and bone marrow. In this case, cancer cells uses a lymphogenous and haematogenous path for spreading and develops primary tumor following by invasion and metastasis.

In case of 4T1 cells injection into the tail vein metastasis manly develops in lung and liver. Such a method simulates haematogenous spreading of tumor cells (Aslakson and Miller, Cancer Res, 1992, 52, 1399-1405; Eckhardt et al, Nat Rev. Drug Discov. 2012, 11, 479-497; Khanna et al, Carcinogenesis 2005, 26, 513-523).

Orthotropic Model of 4T1 Murine Metastatic Breast Cancer with Metastasis in Lung, Liver, Lymph Nodes, and Brain.

Orthotropic model of mouse breast cancer was developed by injection of 4T1 cells in the mammary fat pad of syngeneic BALB/c mice. In this case, 4T1 cells develops solid tumors following by metastasis in lung, liver, lymph nodes, and brain (Aslakson at al., Cancer Res, 1992, 52, 1399-1405).

In our experiments seven-week-old female BALB/c mice were injected orthotopically into the fourth mammary fat pad with $10^5$ 4T1 cells suspended in 0.01 mL of PBS on day zero of the study. The compounds dissolved in DMSO, diluted with 0.1 mL water (DMSO final concentration 1%) and injected s.c. The compounds were administered at 1, 2, 3, 11 days, dose 20 mg/kg. Mice in the untreated group were similarly given four doses of 0.1 mL of water with DMSO. Tumor volume (tumor volume V=47tab2/3, wherein "a" is the maximal, and "b"—the minimal tumor diameter) was calculated twice per week. The mice were examined every other day on appearance, weight and behavior. The mice were sacrificed at day 16 of the experiment by decapitation under ketamine/xylazine anesthesia. After euthanasia, the mice were dissected. The primary tumor, liver and spleen were removed, weighed and studied. All metastases in the internal organs were described.

4T1 Model of Lung Metastasis

Balb/c mice were injected with 100,000 4T1 breath cancer cells into the tail vein and treatment started 24 hr later with subcutaneous (s.c.), intraperitoneal (i.p.) injections or oral administration (p.o.) of compounds according to the following scheme: 1, 4, 7, 9, 11 and 14th days in dose 20 or 40 mg/kg. Compounds were dissolved in DMSO and the solution were diluted by water (DMSO final concentration <1%). Mice in the control group were similarly given doses of 0.1 mL of water with DMSO. Twenty-one days later, all mice were anesthetized with ketamine/xylazine and euthanized, the mice were sacrificed spleens were excised from the mice and weighed. In each experiment, mice were weighed twice weekly.

increase was prevented almost completely (+14%). However, compound I-10 does not affect the development of splenomegaly.

TABLE 5

Inhibitory effects of compounds on experimental lung metastases developed by 4T1 carcinoma cells

| | % of the total area occupied by metastases | | | | | |
|---|---|---|---|---|---|---|
| Compound | Mean ± SD s.c. | % | Mean ± SD p.o. | % | Mean ± SD i.p. | % |
| Control | 50 ± 33 | 100 | | | | |
| I-10 (20 mg/kg) | 10 ± 29 | 19* | 16 ± 18 | 32** | 43 ± 40 | 86 |
| I-11 (20 mg/kg) | 20 ± 30 | 39** | 14 ± 31 | 28** | 31 ± 41 | 62 |
| I-15 (20 mg/kg) | 2 ± 2 | 4* | | | | |
| I-15 (40 mg/kg) | 0 ± 1 | 1* | | | | |

Compounds were administered at 1, 4, 7, 9, 11 and 14th days in dose 20 or 40 mg/kg.
4T1 cells (10,000/0.1 ml PBS) were injected i.v. into syngeneic mice. The number of macroscopic lung metastases was determined 16 days later.
*P < 0.005,
**P < 0.05, compared with control by Student's two-tailed t test.

Enumeration of 4T1 Spontaneous Lung Metastases (India Ink Assay).

(Lewis et al, Cancer Res, 2005, 65) Pulmonary metastases were enumerated by intra-tracheal injection of India ink (15% India Ink, 85% water, 3 drops $NH_4OH$/100 ml). India ink injected lungs were washed in Feket's solution (300 ml 70% EtOH, 30 ml 37% formaldehyde, 5 ml glacial acetic acid) and then placed fresh Feket's solution overnight. Tumor nodules do not absorb India ink, which results in the normal lung tissue staining black and the tumor nodules remaining white. White tumor nodules against a black lung background were measured.

Inhibition of Primary Tumor Growth and Splenomegaly.

The 4T1 orthotropic model closely mimics the progressive forms of estrogen-insensitive human metastatic breast cancer (Heppner et al, Breast Cancer Res 2000, 2, 331-334).

According to our results I-10 and I-11 have significant, but very modest inhibitory effect on the growth of the primary tumor (up to 32%), but surprisingly these compounds dramatically reduces the formation of metastases.

This type of transplantation of tumor cells induces very pronounced splenomegaly. The volume of the spleen in the control group with tumors increased by 316% as compared with healthy animals. In this model, the I-10 and I-11 reduced the development of splenomegaly and increase of spleen weight was 256% and 198% respectively.

Surprisingly, according to our experiments simply magnificent data was received: compounds I-11 and I-15 almost completely (98%) prevents the formation of 4T1 carcinoma lung metastasis in vivo. This effect was observed for each mouse participated in experiment (five in every group) (Table 5, FIG. 2). It should be noted that subcutaneous treatment of compounds was found to be the best.

Figure 2:
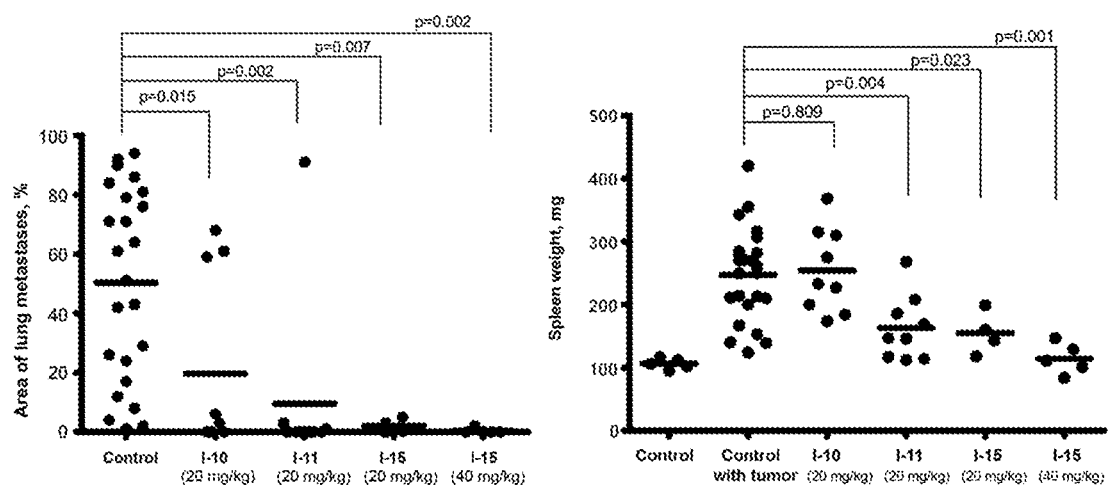
FIG. 2 is a graph demonstrating the inhibition of 4T1 metastasis in lung as well as spleen weight in BALB/c mice. Compounds were administered s.c. at 1, 4, 7, 9, 11 and 14th days. 4T1 cells (10,000/0.1 ml PBS) were injected i.v. into syngeneic mice. The metastasis at day 16 are shown for each mouse, and averages are provided for illustration.

Transplantation of breast cancer tumor cells to mice developed splenomegaly which is associated with the induction of tumor leukemoid reaction and massive granulocytic infiltrates of the red pulp (Johnson et al, Int. J. Cell Cloning, 1985, 3, 91-105; Serafini et al, Cancer Immunol. Immunother., 2004, 53, 64-72; du Pre et al, Experim. Mol. Pathol., 2007, 82, 12-24). The results of spleen weight gain in the animals with tumor is shown in FIG. 2. In the control animals with tumor spleen weight increased by +147%. In the animals treated with I-10 weight gain of spleen was significantly lower (increase by 63%). By the treatment with I-15 in dose 20 mg/kg observed tumor spleen weight increase was only +55% and at the dose of 40 mg/kg—

Those values were particularly encouraging, bearing in mind that these particular selenopheno[h]chromenes did not induce any major side effects either: all animals treated with these compounds looked healthy and active and weight change was visually non-existent.

The performed tests of cytotoxicity and anticancer activity against primary tumor and metastasis of synthesized compounds of Formula 1 on cell lines and on animal models clearly demonstrated, that embodiments of this application are highly active in treatment of cancer metastasis of different localizations even the cytotoxicity of these compounds in vitro is modest. This unexpected discovery together with unprecedentedly high selectivity of compounds towards cancer cells makes these compounds very promising as antimetastatic medicines.

The invention claimed is:

1. A compound of Formula I:

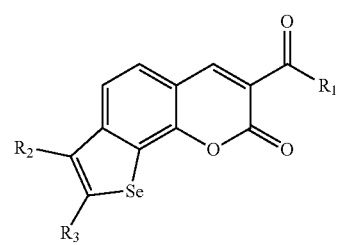

$R_1$ is OH or an $OC_1$-$C_{16}$ hydrocarbon group, wherein the $OC_1$-$C_{16}$ hydrocarbon group is linear, branched or cyclic and is optionally substituted;
$R_2$ represents a halogen; or
$R_3$ is hydroxy-$C_{1-4}$alkyl, 1-hydroxy-cyclo-$C_{3-6}$alkyl, cyclo-$C_{5-7}$alkenyl, hydroxy-$C_{1-6}$cycloalkyl, or $C_{1-4}$alkyl-N-heterocyclyl;
or an optical isomer thereof or a pharmaceutically acceptable acid addition salt thereof.

2. The compound according to claim 1, wherein the compound is selected from the group consisting of:
methyl 7-bromo-8-(2-hydroxypropan-2-yl)-2-oxo-2H-selenopheno[3,2-h]chromene-3-carboxylate, methyl 7-bromo-8-(cyclopent-1-en-1-yl)-2-oxo-2H-selenopheno[3,2-h]chromene-3-carboxylate,
methyl 7-bromo-8-(1-hydroxycyclohexyl)-2-oxo-2H-selenopheno[3,2-h]chromene-3-carboxylate,
methyl 7-bromo-8-(1-methoxycyclohexyl)-2-oxo-2H-selenopheno[3,2-h]chromene-3-carboxylate,
butyl 7-bromo-8-(1-methoxycyclohexyl)-2-oxo-2H-selenopheno[3,2-h]chromene-3-carboxylate,
octyl 7-bromo-8-(1-methoxycyclohexyl)-2-oxo-2H-selenopheno[3,2-h]chromene-3-carboxylate,
decyl 7-bromo-8-(1-methoxycyclohexyl)-2-oxo-2H-selenopheno[3,2-h]chromene-3-carboxylate,
methyl 7-bromo-2-oxo-8-(piperidin-1-ylmethyl)-2H-selenopheno[3,2-h]chromene-3-carboxylate,
methyl 7-bromo-8-(morpholinomethyl)-2-oxo-2H-selenopheno[3,2-h]chromene-3-carboxylate,
methyl 7-bromo-8-((4-methylpiperazin-1-yl)methyl)-2-oxo-2H-selenopheno[3,2-h]chromene-3-carboxylate,
7-bromo-8-(1-hydroxycyclohexyl)-2-oxo-2H-selenopheno[3,2-h]chromene-3-carboxylic acid,
7-bromo-8-(1-methoxycyclohexyl)-2-oxo-2H-selenopheno[3,2-h]chromene-3-carboxylic acid,
7-bromo-2-oxo-8-(piperidin-1-ylmethyl)-2H-selenopheno[3,2-h]chromene-3-carboxylic acid hydrochloride,
7-bromo-2-oxo-8-(morpholin-1-ylmethyl)-2H-selenopheno[3,2-h]chromene-3-carboxylic acid hydrochloride,
7-bromo-8-/(4-methylpiperazin-1-yl)methyl/-2-oxo-2H-selenopheno[3,2-h]chromene-3-carboxylic acid hydrochloride,
Octyl 7-bromo-8-(cyclohex-1-en-1-yl)-2-oxo-2H-selenopheno[3,2-h]chromene-3-carboxylate,
(3S,8S,9S,10R,13R,14S,17R)-10,13-Dimethyl-17-((R)-6-methylheptan-2-yl)-2,3,4,7,8,9,10,11,12,13,14,15,16,17-tetradecahydro-1H-cyclopenta[a]phenanthren-3-yl-7-bromo-8-(cyclohex-1-en-1-yl)-2-oxo-2H-selenopheno[3,2-h]chromene-3-carboxylate,
(3S,8S,9S,10R,13R,14S,17R)-10,13-Dimethyl-17-((R)-6-methylheptan-2-yl)-2,3,4,7,8,9,10,11,12,13,14,15,16,17-tetradecahydro-1H-cyclopenta[a]phenanthren-3-yl-7-bromo-8-(1-methoxycyclohexyl)-2-oxo-2H-selenopheno[3,2-h]chromene-3-carboxylate,
7-Bromo-8-(cyclohex-1-en-1-yl)-3-(piperidine-1-carbonyl)-2H-selenopheno[3,2-h]chromen-2-one,
7-Bromo-8-(cyclohex-1-en-1-yl)-3-(morpholine-1-carbonyl)-2H-selenopheno[3,2-h]chromen-2-one,
7-Bromo-8-(cyclohex-1-en-i-yl)-N,N-bis(2-methoxyethyl)-2-oxo-2H-selenopheno[3,2-h]chromene-3-carboxamide,
7-Bromo-8-(1-methoxycyclohexyl)-3-(morpholine-4-carbonyl)-2H-selenopheno[3,2-h]chromen-2-one,
and pharmaceutically acceptable enantiomers, diastereomers, racemates, and salts thereof.

3. The compound according to claim 2, wherein the compound has the structure:

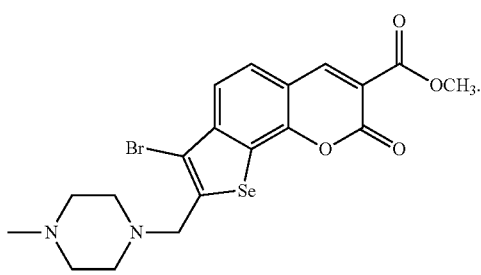 [SMILES: COC(=O)c1cc2ccc3c(Br)c(CN4CCN(C)CC4)[se]c3c2oc1=O]

4. The compound according to claim 2, wherein the compound has the structure:

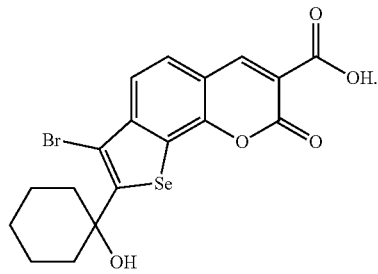 [SMILES: O=C(O)c1cc2ccc3c(Br)c(C4(O)CCCCC4)[se]c3c2oc1=O]

5. The compound according to claim 2, wherein the compound has the structure:

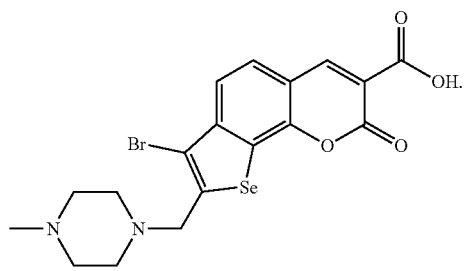 [SMILES: CN1CCN(Cc2[se]c3c(ccc4cc(C(=O)O)c(=O)oc43)c2Br)CC1]

6. A pharmaceutical composition comprising the compound according to claim 1 and a pharmaceutically acceptable carrier.

7. The pharmaceutical composition according to claim 6, wherein the composition is a mono-phasic pharmaceutical composition suitable for parenteral or oral administration, and the composition consists essentially of a therapeutically effective amount of the compound of Formula I, and the pharmaceutically acceptable carrier.

8. A method for the synthesis of a compound of Formula I:

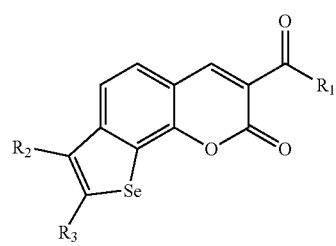

wherein
$R_1$ represents OH or a $OC_1$-$C_{16}$ hydrocarbon group, wherein the $OC_1$-$C_{16}$ hydrocarbon group is linear, branched or cyclic and is optionally substituted;
$R_2$ represents a halogen;
$R_3$ represents hydroxy-$C_{1-4}$alkyl, 1-hydroxy-cyclo-$C_{3-6}$alkyl, cyclo-$C_{5-7}$alkenyl, hydroxy-$C_{1-6}$cycloalkyl, or $C_{1-4}$alkyl-N-heterocyclyl;
comprising reacting a compound of formula II with a selenium halide:

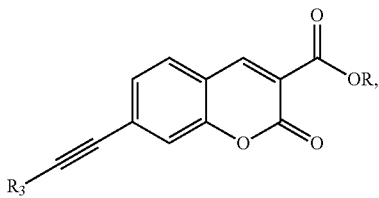

wherein

R represents $C_1$-$C_{10}$ hydrocarbon group.

9. The method of claim 8, wherein reacting the compound of formula II with a selenium halide forms a compound of formula III:

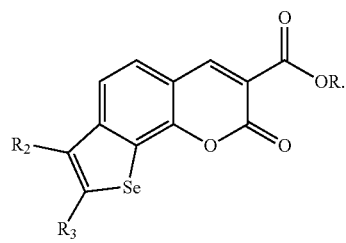

10. The method of claim 9, further comprising subjecting the compound of formula III to hydrolyzation to form a compound of formula I, in which $R_1$ is OH.

11. The method of claim 10, further comprising subjecting the compound of formula I in which $R_1$ is OH to esterification to form a compound of formula I in which $R_1$ is an $OC_1$-$C_{16}$ hydrocarbon group.

12. The compound of claim 1, wherein $R_1$ is an $OC_1$-$C_{16}$ hydrocarbon group optionally substituted by a steroid moiety, N(alkyl)$_2$, or N-heterocyclyl.

13. The compound of claim 1, wherein $R_1$ is OH or $OCH_3$.

14. The compound of claim 1, wherein $R_2$ is Br.

15. The compound of claim 1, wherein $R_3$ is 1-hydroxy-cyclo-$C_{3-6}$alkyl, hydroxy-$C_{1-6}$cycloalkyl, or $C_{1-4}$alkyl-N-heterocyclyl.

16. A method for the treatment of cancer or metastasis of cancer, comprising administering to an individual in need thereof a therapeutically effective amount of the compound of claim 1;

wherein the cancer is melanoma, breast adenocarcinoma, sarcoma, fibrosarcoma, lung cancer, hepatocellular carcinoma, and neuroblastoma.

17. The method of claim 16, wherein the compound is administered in conjunction with one or more chemotherapeutic agents, surgery, chemotherapy, radiation, immunotherapy, or combinations thereof.

* * * * *

UNITED STATES PATENT AND TRADEMARK OFFICE
CERTIFICATE OF CORRECTION

PATENT NO. : 10,561,681 B2
APPLICATION NO. : 16/315264
DATED : February 18, 2020
INVENTOR(S) : Pavels Arsenjans et al.

It is certified that error appears in the above-identified patent and that said Letters Patent is hereby corrected as shown below:

Column 33, Line 46, Claim 2, delete, "-en-i-yl)" and insert -- -en-1-yl) --.

Signed and Sealed this
Seventh Day of April, 2020

Andrei Iancu
*Director of the United States Patent and Trademark Office*